US012570726B2

(12) United States Patent
Tomita et al.

(10) Patent No.: US 12,570,726 B2
(45) Date of Patent: Mar. 10, 2026

(54) ANTI-HIV ANTIBODY AND METHOD FOR PRODUCING SAME

(71) Applicants: Immuno-Biological Laboratories Co., Ltd., Fujioka (JP); National University Corporation Kumamoto University, Kumamoto (JP); CURED Inc., Yokohama (JP); National Institutes of Biomedical Innovation, Health and Nutrition, Ibaraki (JP)

(72) Inventors: Masahiro Tomita, Fujioka (JP); Mamoru Shimizu, Fujioka (JP); Shuzo Matsushita, Kumamoto (JP); Takeo Kuwata, Kumamoto (JP); Masahiro Michishita, Yokohama (JP); Yasuhiro Yasutomi, Tsukuba (JP); Tomotaka Okamura, Tsukuba (JP)

(73) Assignee: Immuno-Biological Laboratories Co. Ltd., Fujioka-Shi, MA (US)

( * ) Notice: Subject to any disclaimer, the term of this patent is extended or adjusted under 35 U.S.C. 154(b) by 929 days.

(21) Appl. No.: 17/290,054

(22) PCT Filed: Oct. 28, 2019

(86) PCT No.: PCT/JP2019/042184
§ 371 (c)(1),
(2) Date: Apr. 29, 2021

(87) PCT Pub. No.: WO2020/090747
PCT Pub. Date: May 7, 2020

(65) Prior Publication Data
US 2022/0002389 A1     Jan. 6, 2022

(30) Foreign Application Priority Data

Oct. 29, 2018   (JP) ................................. 2018-203114
Sep. 12, 2019   (JP) ................................. 2019-166040

(51) Int. Cl.
*C07K 16/10*         (2006.01)
*A01K 67/35*         (2025.01)
(52) U.S. Cl.
CPC .......... *C07K 16/1045* (2013.01); *A01K 67/35* (2025.01); *A01K 2217/05* (2013.01); *A01K 2227/706* (2013.01); *A01K 2267/01* (2013.01); *C07K 2317/20* (2013.01); *C07K 2317/41* (2013.01); *C07K 2317/565* (2013.01)
(58) Field of Classification Search
CPC ........... C07K 16/1045; C07K 2317/20; C07K 2317/41; C07K 2317/565; A01K 67/04; A01K 2217/05; A01K 2227/706; A01K 2267/01
See application file for complete search history.

(56) References Cited

U.S. PATENT DOCUMENTS

| | | | |
|---|---|---|---|
| 6,114,143 A | 9/2000 | Eda | |
| 6,602,684 B1 | 8/2003 | Umana et al. | |
| 8,722,861 B2 * | 5/2014 | Matsushita | ........ C07K 16/1045 424/160.1 |
| 9,169,318 B2 * | 10/2015 | Horowitz | ............. A61K 39/145 |
| 9,447,167 B2 * | 9/2016 | Sekiguchi | .............. C07K 14/75 |
| 12,173,052 B2 * | 12/2024 | Diskin | .............. C07K 16/1045 |
| 12,410,243 B2 * | 9/2025 | Chan-Hui | .......... C07K 16/1045 |
| 2007/0083940 A1 * | 4/2007 | Yoshizato | .......... A01K 67/0339 800/8 |
| 2008/0301823 A1 * | 12/2008 | Tomita | ................... A01K 67/04 536/23.7 |
| 2011/0044995 A1 | 2/2011 | Matsushita et al. | |
| 2011/0203009 A1 * | 8/2011 | Tomita | ................... A01K 67/04 435/348 |
| 2014/0005368 A1 | 1/2014 | Helman et al. | |
| 2016/0002319 A1 | 1/2016 | Killian | |
| 2016/0032010 A1 * | 2/2016 | Shirai | ...................... C12Q 1/37 435/68.1 |
| 2022/0347263 A1 * | 11/2022 | Glenn | ...................... A61P 31/14 |
| 2025/0066457 A1 * | 2/2025 | Diskin | .............. C07K 16/1063 |

FOREIGN PATENT DOCUMENTS

| | | |
|---|---|---|
| CN | 108699131 | 10/2018 |
| JP | 2014012024 A | 1/2014 |
| JP | 2017079775 A | 5/2017 |

(Continued)

OTHER PUBLICATIONS

Scamurra et al. GenBank: AAQ05693.1. Direct Submission. Submitted Jan. 22, 2002. (Year: 2002).*

(Continued)

*Primary Examiner* — Janet L Andres
*Assistant Examiner* — Carey Alexander Stuart
(74) *Attorney, Agent, or Firm* — FisherBroyles, LLP

(57)     ABSTRACT

The present inventors have conducted intensive studies on an antibody which controls HIV in an administration group with a high probability over a long period of time with one or several times of single-agent administration. As a result, the present inventors have surprisingly found that, when an SW-1C10 antibody, which is obtained by producing an antibody gene reported as 1C10 in silkworms, is singly administered only a few times, the viral load in the blood is suppressed to the detection limit or lower at an early stage in all of individuals to which the antibody has been administered, and moreover, the viral RNA load in the blood is maintained at the detection limit or lower for a long time of 12 weeks.

17 Claims, 6 Drawing Sheets

Specification includes a Sequence Listing.

(56) References Cited

FOREIGN PATENT DOCUMENTS

| WO | WO-2008032748 A1 * | 3/2008 | ......... A01K 67/0335 |
| WO | 2009066702 A1 | 4/2011 | |
| WO | WO-2021065846 A1 * | 4/2021 | |

OTHER PUBLICATIONS

Vander Heiden et al. GenBank: MCC86771.1. Direct Submission. Submitted Apr. 9, 2018. (Year: 2018).*

Johnson et al. GenBank: AXP31635.1. Direct Submission. Submitted May 26, 2018. (Year: 2018).*

Ramirez et al. GenBank: AIZ68509.1. Direct Submission. Submitted Sep. 23, 2014. (Year: 2014).*

Horowitz et al. GenBank: AOC48785.1. Aug. 15, 2016. (Year: 2016).*

Bowie JU, Reidhaar-Olson JF, Lim WA, Sauer RT. Deciphering the message in protein sequences: tolerance to amino acid substitutions. Science. Mar. 16, 1990;247(4948):1306-10 (Year: 1990).*

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14 (Year: 2000).*

Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714 (Year: 2015).*

Sela-Culang I, Kunik V, Ofran Y. The structural basis of antibody-antigen recognition. Front Immunol. Oct. 8, 2013;4:302. (Year: 2013).*

Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2016).*

Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*

Collis, A. V., Brouwer, A. P., & Martin, A. C. (2003). Analysis of the antigen combining site: correlations between length and sequence composition of the hypervariable loops and the nature of the antigen. Journal of molecular biology, 325(2), 337-354. (Year: 2003).*

Dondelinger M, Filée P, Sauvage E, Quinting B, Muyldermans S, Galleni M, Vandevenne MS. Understanding the Significance and Implications of Antibody Numbering and Antigen-Binding Surface/Residue Definition. Front Immunol. Oct. 16, 2018;9:2278. (Year: 2018).*

Tan, H. et al. (2023). Large-scale and cost-effective production of recombinant human serum albumin (rHSA) in transgenic Bombyx mori cocoons. International journal of biological macromolecules, 245, 125527. (Year: 2023).*

Yamano, M. et al. (2022) Bioengineered Silkworm for Producing Cocoons with High Fibroin Content for Regenerated Fibroin Biomaterial-Based Applications. International journal of molecular sciences, 23(13), 7433. (Year: 2022).*

Heryanto, C., Mazo-Vargas, A., & Martin, A. (2022). Efficient hyperactive piggyBac transgenesis in *Plodia pantry* moths. Frontiers in genome editing, 4, 1074888.*

Saphire, E.O. et al. (2001). (2001). Crystal Structure of a Neutralizing Human IgG against HIV-1: A Template for Vaccine Design. Science (American Association for the Advancement of Science), 293(5532), 1155-1159. (Year: 2001).*

Lorin, V. et al. (2022). Epitope convergence of broadly HIV-1 neutralizing IgA and IgG antibody lineages in a viremic controller. The Journal of Experimental Medicine, 219(3). (Year: 2022).*

Zolla-Pazner, S. et al. (2014). Vaccine-induced IgG antibodies to V1V2 regions of multiple HIV-1 subtypes correlate with decreased risk of HIV-1 infection. PloS One, 9(2), e87572-e87572. (Year: 2014).*

Chen, W. et al. (2018). Transgenic Silkworm-Based Silk Gland Bioreactor for Large Scale Production of Bioactive Human Platelet-Derived Growth Factor (PDGF-BB) in Silk Cocoons. International journal of molecular sciences, 19(9), 2533. (Year: 2018).*

Kong, L. et al. (2013). Supersite of immune vulnerability on the glycosylated face of HIV-1 envelope glycoprotein gp120. Nature Structural & Molecular Biology, 20(7), 796-803. (Year: 2013).*

Li, L., Chen, S., Miao, Z., Liu, Y., Liu, X., Xiao, Z. X., & Cao, Y. (2019). AbRSA: A robust tool for antibody numbering. Protein science : a publication of the Protein Society, 28(8), 1524-1531. (Year: 2019).*

Matsushita et al. 2021. WO 2021065846 A1. Machine translation. (Year: 2021).*

Walker LM et al. Broad neutralization coverage of HIV by multiple highly potent antibodies. Nature. Sep. 22, 2011;477(7365):466-70. (Year: 2011).*

Walker LM et al. Supplemental Information: Broad neutralization coverage of HIV by multiple highly potent antibodies. Nature. Sep. 22, 2011;477(7365):466-70. (Year: 2011).*

Izuka et al.; "Production of a recombinant mouse monoclonal antibody in transgenic silkwork cocoons"; the FEBS Journal 276, The Authors Journal Compilation; pp. 1-15; (2009).

Tada et al.; "Characterization of anti-CD20 monoclonal antibody produced by transgenic silkworms (*Bombyx mori*)"; mAbs 7:6, Nov./Dec. 2015; Published with license by Taylor & Francis Group, LLC; vol. 7 Issue 6; pp. 1-13 (2015).

Barouch et al.; "Therapeutic Efficacy of Potent Neutralizing HIV-1-Specific Monoclonal Antibodies in SHIV-Infected Rhesus Monkeys"; HHS Public Access, Author Manuscript; pp. 1-24; (2015).

Valdez et al.; "Complementary and synergistic activities of anti-V3, CD4bs and CD4i antibodies derived from a single individual can cover a wide range of HIV-1 strains"; Elsevier, www.elsevier.com/locate/yviro; pp. 1-17; (2015).

Press release described on the website of Immuno-Biological Laboratories Co., Ltd. on Mar. 16, 2018, the conclusion of the contract of the joint development with Cured Inc. [online], Immuno-Biological Laboratories Co., Ltd., Mar. 26, 2018 [retrieved on Nov. 15, 2019], internet :<URL: japan.co.jp/direct/topics/topics_pdf_download/topics_id=4947&disp=inline>, in particular, summary (2018).

Nishimura et. al.; Early antibody therapy can induce long-lasting immunity to SHIV., Nature, 2017, 543, pp. 559-563, in particular, p. 559, left column, first paragraph, right column, fifth column, fig. 1; pp. 1-21; (2017).

Desikan et. al.; "Early exposure to broadly neutralizing antibodies triggers a switch from progressive disease to asting control of SHIV infection, bioRxiv preprint", [online], Feb. 13, 2019, [retrieved on Nov. 15, 2019], <URL:https://www.biorxiv.org/content/biorxiv/early/2019/10/13/548727.full.pdf>, in particular, abstract (2019).

Japanese Patent Office; International Search Report; PCT Application No. PCT/JP2019/042184; (machine translation); pp. 1-2 (mailed Oct. 20, 2020).

Japanese Patent Office; Written Opinion of the International Preliminary Examining Authority (Form PCT/IPEA/408); PCT Application No. PCT/JP2019/042184; (machine translation); pp. 1-12; Mailing Date: (Oct. 20, 2020).

Japanese Patent Office; International Preliminary Report on Patentability; (Form PCT/IPEA/409); PCT Application No. PCT/JP2019/042184; pp. 1-10; (mailing date: Apr. 29, 2021).

Lazar et. al.; "Engineered antibody Fc variants with enhanced effector function", PNAS, Mar. 14, 2006, vol. 103. No. 11, 4005-4010; www.pnas.org/cgi/doi/10.1073/pnas.0508123103; pp. 1-6 (2006).

Stavenhagen et. al., "Fc Optimization of Therapeutic Antibodies Enhances Their Ability to Kill Tumor Cells In vitro and Controls Tumor Expansion In vivo via Low-Affinity Activating Fcγ Receptors", American Associate for Cancer Research; 67: (18). Sep. 15, 2007; 8882-8890; www.aacrjournals.org; pp. 1-10 (2007).

Barouch et al.; "Therapeutic Efficacy of Potent Neutralizing HIV-1-Specific Monoclonal Antibodies in SHIV-Infected Rhesus Monkeys"; HHS Public Access, Author Manuscript; pp. 1-24; (2013).

Japanese Patent Office; International Search Report; PCT Application No. PCT/JP2019/042184; (machine translation); pp. 1-2 (mailed Dec. 3, 2019).

(56)         References Cited

OTHER PUBLICATIONS

Japanese Patent Office; "Notice of Reasons for Rejection" dated Jun. 11, 2024; Japanese Patent Application No. 2020-553897; pp. 1-20 (English & Japanese); pp. 1-20 (2024).

Folia pharmacologica Japonica, 2016, vol. 147, No. 4, p. 235-240 (Japanese only—concise explanation of relevance in English translation of "Notice of Reasons for Rejection"); pp. 1-7 (2016).

Yakugaku Zasshi, "Potelligent Antibodies as Next Generation Therapeutic Antibodies"; 2009, vol. 129, No. 1, p. 3-9 (concise explanation of relevance in English translation of "Notice of Reasons for Rejection"); pp. 1-8 (2009).

Frontier of Development of Antibody Medicine, CMC Publishing Co., Ltd., 2007, p. 176-181; (Japanese only—concise explanation of relevance in English translation of "Notice of Reasons for Rejection"); pp. 1-8 (2007).

Kristel Paola Ramirez Valdez et al.; "Complementary andsynergisticactivitiesofanti-V3, CD4bs and CD4i antibodies derived from a single individua; I can cover a wide range of HIV-1 strains"; Elevier; www.elsevier.com/locate/yviro; Virology 475 (2015) 187-203; (Year: 2014).

Tada et al. "Characterization of anti-CD20 monoclonal antibody produced by transgenic silkworms (*Bombyx mori*)"; http://dx.doi.org/10.1080/19420862.2015.1078054; mAbs, 7:6, 1138-1150, ISSN: 1942-0862 (Print) 1942-0870 (Online) Journal homepage: http://www.tandfonline.com/loi/kmab20; (Year: 2015).

Kristel Paola Ramirez Valdez et al. (2015)—Supplementary Materials for "Complementary andsynergisticactivitiesofanti-V3, CD4bs and CD4i antibodies derived from a single individua; I can cover a wide range of HIV-1 strains"; Elevier; www.elsevier.com/locate/yviro; Virology 475 (2015) 187-203; (Year: 2014), 8 pages.

European Patent Office; "Extended European Search Report" dated Jun. 15, 2022; EPO Application No. 19879893.6; pp. 1-16 (2022).

Xueling Wu et al: "Rational design of envelope identifies broadly neutralizing human monoclonal antibodies to HIV-1", Science, American Association for the Advancement of Science, US, vol. 329, No. 5993, Aug. 13, 2010 (Aug. 13, 2010), pp. 856-861, XP002669441, ISSN: 0036-8075, DOI: 10.1126/SCIENCE. 1187659; [retrieved on Jul. 8, 2010]* abstract, figures 1-4 (2010).

Okazaki A et al: "Fucose Depletion from Human IgG1 Oligosaccharide Enhances Binding Enthalpy and Association Rate Between IgG1 and FcgammaRIIIa", Journal of Molecular Biology, Academic Press, United Kingdom, vol. 336, No. 5, Mar. 5, 2004 (Mar. 5, 2004) , pp. 1239-1249, XP004490178, ISSN: 0022-2836, DOI: 10.1016/J.JMB.2004.01.007 * abstract * (2004).

Shinkawa T et al: "The absence of fucose but not the presence of galactose or bisecting N-acetylglucosamine of human IgG1 complex-type oligosaccharides shows the critical role of enhancing antibody-dependent cellular cytotoxicity", Journal of Biological Chemistry, American Society for Biochemistry and Molecular Biology, US, vol. 278, No. 5, Jan. 31, 2003 (Jan. 31, 2003), pp. 3466-3473, XP002355427, ISSN: 0021-9258, DOI: 10.1074/JBC. M210665200 * abstract, figure 2 * (2003).

Mathieu Dondelinger et al: "Understanding the Significance and Implications of Antibody Numbering and Antigen-Binding Surface/Residue Definition", Frontiers in Immunology, vol. 9, Oct. 16, 2018 (Oct. 16, 2018), pp. 1-15, XP055572450, DOI: 10.3389/fimmu. 2018.02278; * abstract, pp. 3-7, fig. 6; (2018).

* cited by examiner

ALL EXTRACTION        NEUTRAL BUFFER SOLUTION

- ◆ BaL-NKR:CRD-H01
- ● BaL-NKR:293A-1C10
- ■ NKR24:CRD-H01
- ✳ NKR24:293A-1C10

* MFI : mean fluorescence intensity
* BaL-NKR: BaL-infected NKR24
  NKR24 (Normal) :uninfected NKR24

| Ab (µg/mL) | %inhibition | | | |
|---|---|---|---|---|
| | SW | Bcell | 293A | CHO |
| 4 | 98.84% | 99.07% | 98.82% | 99.15% |
| 0.8 | 92.44% | 92.51% | 89.87% | 94.92% |
| 0.16 | 65.38% | 63.40% | 54.38% | 69.76% |
| 0.032 | 12.37% | 23.84% | 19.55% | 27.35% |
| 0.0064 | 13.67% | 8.70% | 2.96% | 1.21% |
| 0.00128 | -1.79% | 3.21% | 8.12% | 8.08% |
| 0.000256 | 8.51% | 7.67% | -0.79% | 6.95% |
| 0.0000512 | -4.43% | 2.24% | 2.98% | -4.96% |

*FIG. 4*

| | | 1C10 DERIVED FROM SILKWORM (SW-1C10) | | 1C10 DERIVED FROM CHO (CHO-1C10) | |
|---|---|---|---|---|---|
| GLYCAN CONTAINING NO FUCOSE | | 1.6% | 97.7% | 0% | 24.9% |
| | | 14.5% | | 2.1% | |
| | | 6.0% | | 2.2% | |
| | | 1.6% | | 0% | |
| | | 66.1% | | 16.4% | |
| | | 5.1% | | 1.6% | |
| | | 1.4% | | 0.6% | |
| | | 1.4% | | 0% | |
| GLYCAN CONTAINING FUCOSE | | 0% | 0% | 0.6% | 70.2% |
| | | 0% | | 13.0% | |
| | | 0% | | 52.3% | |
| | | 0% | | 0.7% | |
| | | 0% | | 3.1% | |
| | | 0% | | 0.6% | |
| OTHERS | | 2.3% | 2.3% | 4.8% | 4.8% |

■ : N-ACETYLGLUCOSAMINE
● : MANNOSE
● : GALACTOSE
▶ : FUCOSE

| Ab | 1C10 | | | KD-247 (%killing) |
|---|---|---|---|---|
| conc. (µg/mL) | SW (%killing) | 293A (%killing) | CHO (%killing) | |
| 0.2 | 21.5 | 0 | 11.7 | 0 |
| 2 | 40.1 | 2.4 | 30.7 | 1.8 |
| 20 | 57.2 | 8.6 | 47.7 | 20.9 |

Target cells: BaL-infected NKR24
Effector cells: N6

*FIG. 6*

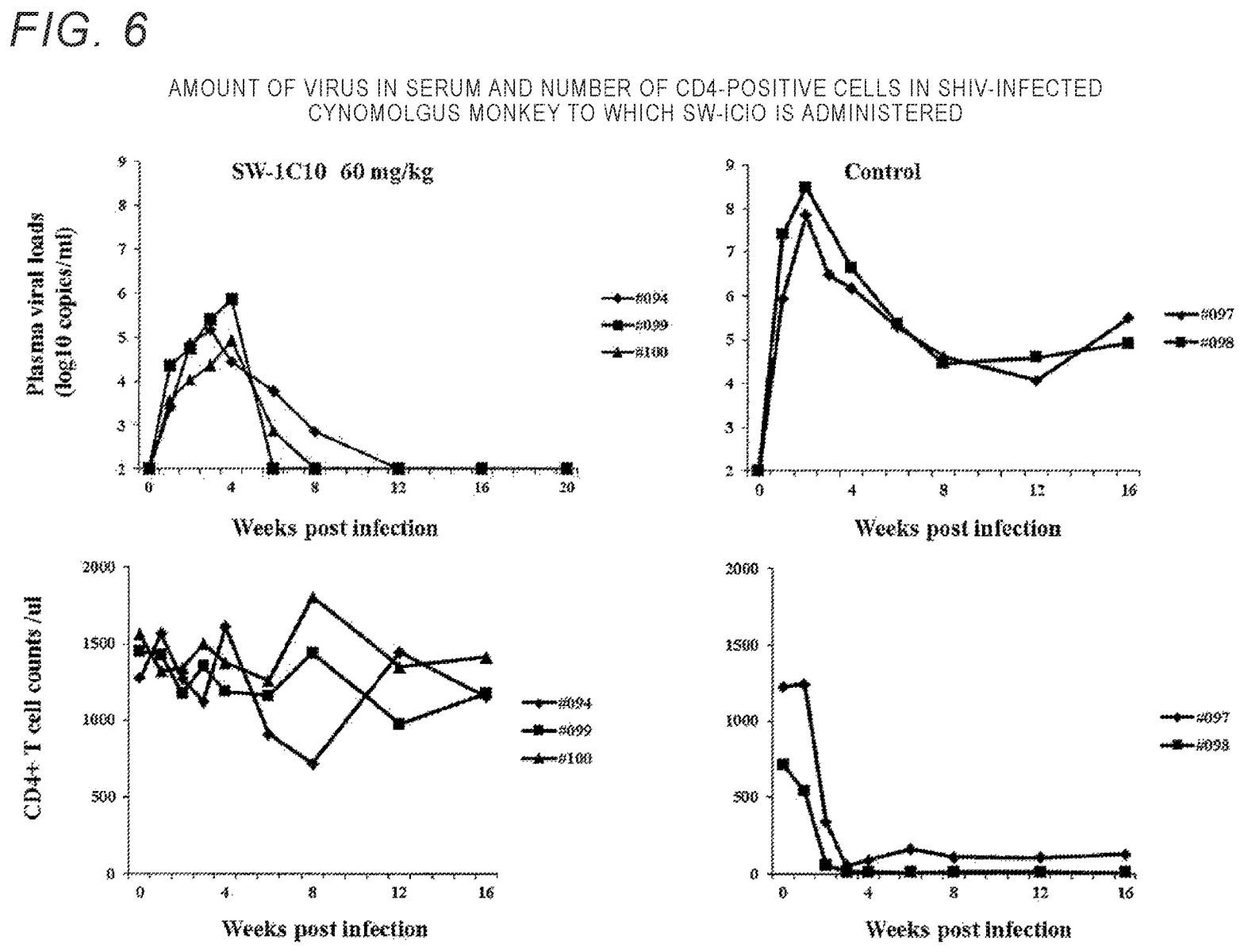

AMOUNT OF VIRUS IN SERUM AND NUMBER OF CD4-POSITIVE CELLS IN SHIV-INFECTED CYNOMOLGUS MONKEY TO WHICH SW-1CI0 IS ADMINISTERED

ANTI-HIV ANTIBODY AND METHOD FOR PRODUCING SAME

CROSS REFERENCE TO RELATED APPLICATIONS

This international patent application claims the priority based on Japanese Patent Application No. 2018-203114 filed on Oct. 29, 2018, and Japanese Patent Application No. 2019-166040 filed on Sep. 12, 2019, the entire contents of which are hereby incorporated by reference.

TECHNICAL FIELD

The present invention relates to a method for efficiently producing an anti-HIV antibody. More specifically, the present invention relates to a method for producing an anti-HIV antibody with high efficiency by utilizing silkworms.

BACKGROUND ART

An attempt has been made to place an antibody gene downstream of the sericin promoter of silkworms to express an antibody molecule in the cocoons, thereby producing a therapeutic antibody with silkworms (for example, Non-Patent Documents 1 and 2). In particular, an antibody expressed in the cocoons of silkworms, which contains no core fucose in the glycans, has been known to exhibit an excellent ADCC activity (Patent Documents 1 and 2).

Also, in the therapeutic strategy of HIV, an antibody has been expected that enables to control HIV over a long period of time with one or several times of administration of the antibody. For example, Non-Patent Document 3 reports that, among four rhesus macaques to which PGT121 has been administered once, the viral RNA load is suppressed to the detection limit or lower over about 70 days in one rhesus macaque.

Further, KD247, which is a humanized antibody recognizing the V3 loop of gp120 which is envelope protein of HIV, has been developed and a clinical test thereof has been conducted. In a patient to which KD247 has been administered three times, suppression of the viral load is confirmed. However, suppression of the viral load to the detection limit or lower for a long period of time is not achieved. As described above, an antibody that can suppress the viral load to the detection limit or lower with a high probability for a long period of time with one to several times of single-agent administration has not been developed.

In view of the above circumstances, development of a 1C10 antibody, which is a human antibody having an antigen recognition site same as KD247 has proceeded. The 1C10 antibody is an antibody that is isolated from a patient having antibodies capable of neutralizing a wide range of HIV strains, whose symptom has been suppressed without any treatment for a long period of more than 25 years. The 1C10 antibody has been expected to exhibit a high therapeutic effect by being administered to an HIV-infected patient as a therapeutic antibody (Patent Document 2 and Non-Patent Document 4).

PRIOR ART DOCUMENTS

Patent Documents

Patent Document 1: Japanese Unexamined Patent Application Publication No. 2014-12024

Patent Document 2: International Patent Publication No. WO2009/066702

Non-Patent Documents

Non-Patent Document 1: Masashi Iizuka, et al., FEBS Journal; 276:5806-5820(2009)
Non-Patent Document 2: Minoru Toda, et al., mABs; 7(6) 1138-1150(2015)
Non-Patent Document 3: Dan H. Barouch, et al., Nature; 503(7475):224-228(2013)
Non-Patent Document 4: Kristel Paola Ramirez Valdez, et al., Virology; 475:187-203(2015)

SUMMARY OF THE INVENTION

The present inventors have conducted intensive studies on an antibody which highly probably controls HIV in an administration group over a long period of time with one or several times of single-agent administration. As a result, the inventors have surprisingly found that, small number of times of administration of SW-1C10 antibody, which is obtained by producing an antibody from a gene reported as 1C10 in silkworms, not only suppressed the viral load in the blood below the detection limit at an early stage in all of administered individuals, but also the viral RNA load in the blood is maintained below the detection limit for such a long time as 12 weeks. Further, the inventors have compared an antibody produced in silkworms and an antibody produced in CHO cells to confirm that the structural difference between these antibodies exists in their glycan structures. In view of the above, the present inventors have concluded that removal of fucose from glycans make the 1C10 antibody to have an extremely excellent activity in suppressing the viral load for a long period of time in all administered cases. It has not been reported in the past that viral replication can be suppressed over a long period of time in all administered cases. The inventors, for the first time, have succeeded in discovering an antibody that can widely and stably suppresses the viral load in an administered subject with a few times of single-agent administration.

Further, the yield of the antibody in silkworms was approximately several hundreds μg per cocoon, or several μg per 1 mg of cocoon in the past, but no study have been conducted to increase the productivity to yield more than this level. The inventors have conducted studies to find an anti-HIV antibody having a higher yield in silk-spinning insects among a large number of anti-HIV antibodies. As a result, the inventors have found that anti-HIV antibodies, 1C10 antibody and 1D9 antibody, are produced in silk threads of silk-spinning insects at a higher yield than the previously obtained yield, and thus have completed the present invention.

Accordingly, in an embodiment, the present invention relates to an antibody, wherein the antibody has a binding ability to HIV; glycans bound to the antibody contain no fucose; and the antibody has an activity of suppressing HIV load in the blood of an HIV-infected patient below a detection limit at a probability of 90% or more with one or several times of administration to the HIV-infected patient. A method for examining whether a given antibody has a binding ability to HIV has been widely known in the technical field. The ability can be confirmed by, for example, bringing the antibody into contact with a carrier to which HIV is immobilized and detecting the antibody bound to the carrier.

In an embodiment, the present invention relates to an IgG antibody, wherein the antibody has a heavy chain comprising the amino acid sequence of SEQ ID NO: 7, an amino acid sequence having 80% or more identity with the amino acid sequence of SEQ ID NO: 7, or an amino acid sequence in which several amino acids are substituted, deleted, added, and/or inserted in the amino acid sequence of SEQ ID NO: 7, and a light chain comprising the amino acid sequence of SEQ ID NO: 9, an amino acid sequence having 80% or more identity with the amino acid sequence of SEQ ID NO: 9, or an amino acid sequence in which several amino acids are substituted, deleted, added, and/or inserted in the amino acid sequence of SEQ ID NO: 9; the antibody has a binding ability to HIV; and glycans bound to the antibody contain no fucose.

Preferably, in the antibody of the present invention, the heavy chain has the three CDR sequences in the heavy chain amino acid sequence of SEQ ID NO: 7, and the light chain has the three CDR sequences in the amino acid sequence of SEQ ID NO: 9. A determination of the CDR sequence can be conducted by referring to the numbering system of Kabat et al. (Kabat, E. et al., U.S. Department of Health and Human Services, (1983) and later versions), the numbering system of Chothia et al. (Chothia and Lesk, J. Mol. Biol., 196: 901-917 (1987)), the numbering system of Honegger et al. (Honegger, A et al., . Mol. Biol. 309: 657-670 (2001)), the contact determination method (MacCallum et al., J Mol Biol. 262(5): 732-745 (1996)), the numbering system according to the IMGT database, or alignment to known sequence databases. The CDR sequence of the antibody of the present invention can be, for example, CDRH1: GFMFSNYA (SEQ ID NO: 14); CDRH2: ISNDGSDK (SEQ ID NO: 15); and CDRH3: CARDLDQTIPDL-TAPAFEV (SEQ ID NO: 16), and CDRL1: QSLLHSDGNN (SEQ ID NO: 17); CDRL2: LTS (SEQ ID NO: 18); and CDRL3: MQSLQTWT (SEQ ID NO: 19). More preferably, the antibody of the present invention has a heavy chain consisting of the amino acid sequence of SEQ ID NO: 7 and a light chain consisting of the amino acid sequence of SEQ ID NO: 9.

In the antibody of the present invention, no fucose is contained in glycans attached to the antibody. The antibody of the present invention may have a glycan structure selected from the following formulas, for example.

[Formula 1]

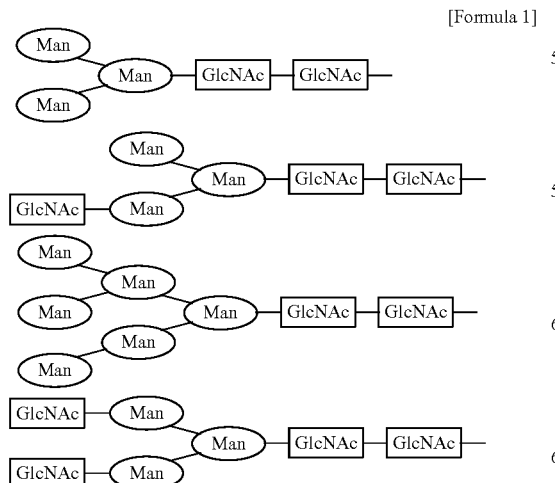

-continued

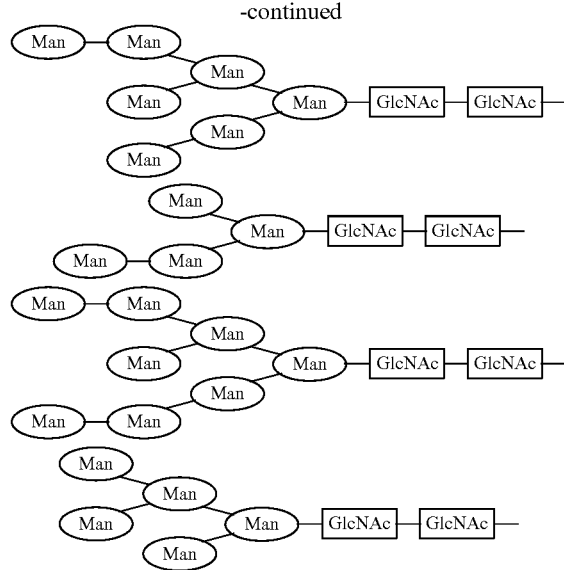

In an embodiment, the present invention relates to an expression cassette containing any one polynucleotide selected from the following (i) to (x) which is functionally linked to downstream of a silk gland-specific gene promoter:

(i) a polynucleotide having the nucleotide sequence of SEQ ID NO: 6 and/or the nucleotide sequence of SEQ ID NO: 8;

(ii) a polynucleotide having a nucleotide sequence which hybridizes with the nucleotide sequence of SEQ ID NO: 6 under a stringent condition and/or a nucleotide sequence which hybridizes with the nucleotide sequence of SEQ ID NO: 8 under a stringent condition;

(iii) a polynucleotide encoding the amino acid sequence of SEQ ID NO: 7, and/or a polynucleotide encoding the amino acid sequence of SEQ ID NO: 9;

(iv) a polynucleotide encoding an amino acid sequence having 80% or more identity with the amino acid sequence of SEQ ID NO: 7, and/or a polynucleotide encoding an amino acid sequence having 80% or more identity with the amino acid sequence of SEQ ID NO: 9;

(v) a polynucleotide encoding an amino acid sequence in which several amino acids are substituted, deleted, added, and/or inserted in the amino acid sequence of SEQ ID NO: 7, and/or a polynucleotide encoding an amino acid sequence in which several amino acids are substituted, deleted, added, and/or inserted in the amino acid sequence of SEQ ID NO: 9;

(vi) a polynucleotide having the nucleotide sequence of SEQ ID NO: 10 and/or the nucleotide sequence of SEQ ID NO: 12;

(vii) a polynucleotide having a nucleotide sequence which hybridizes with the nucleotide sequence of SEQ ID NO: 10 under a stringent condition and/or a nucleotide sequence which hybridizes with the nucleotide sequence of SEQ ID NO: 12 under a stringent condition;

(viii) a polynucleotide encoding the amino acid sequence of SEQ ID NO: 11, and/or a polynucleotide encoding the amino acid sequence of SEQ ID NO: 13;

(ix) a polynucleotide encoding an amino acid sequence having 80% or more identity with the amino acid sequence of SEQ ID NO: 11, and/or a polynucleotide encoding an amino acid sequence having 80% or more identity with the amino acid sequence of SEQ ID NO: 13; and (x) a polynucleotide encoding an amino acid sequence in which several amino acids are substituted, deleted, added, or inserted in the amino acid sequence of SEQ ID NO: 11, and/or a polynucleotide encoding an amino acid sequence in which several amino acids are substituted, deleted, added, and/or inserted in the amino acid sequence of SEQ ID NO: 13.

In the present specification, the 1C10 antibody is an antibody having a heavy chain consisting of the amino acid sequence of SEQ ID NO: 7 and a light chain consisting of the amino acid sequence of SEQ ID NO: 9. In the amino acid sequence of SEQ ID NO: 7, the positions 1 to 19 constitute of a signal sequence. The heavy chain and/or light chain of the antibody described in the present specification may not include the signal sequence described in the present specification. Alternatively, the heavy chain and/or light chain may include a signal sequence other than the signal sequence described in the present specification. Accordingly, in the present specification, the wording "heavy chain consisting of the amino acid sequence of SEQ ID NO: 7" may be interchangeably read as "heavy chain consisting of the amino acid sequence at positions 20 to 474 in the amino acid sequence of SEQ ID NO: 7". Similarly, in the amino acid sequence of SEQ ID NO: 9, the positions 1 to 20 constitute of a signal sequence. Accordingly, in the present specification, the wording "light chain consisting of the amino acid sequence of SEQ ID NO; 9" may be interchangeably read as "light chain consisting of the amino acid sequence at positions 21 to 238 in the amino acid sequence of SEQ ID NO: 9". In the present specification, the 1D9 antibody is an antibody having a heavy chain consisting of the amino acid sequence of SEQ ID NO: 11 and a light chain consisting of the amino acid sequence of SEQ ID NO: 13. In the amino acid sequence of SEQ ID NO: 11, the positions 1 to 19 constitute of a signal sequence. Accordingly, in the present specification, the wording "heavy chain consisting of the amino acid sequence of SEQ ID NO: 11" may be interchangeably read as "heavy chain consisting of the amino acid sequence at positions 20 to 472 in the amino acid sequence of SEQ ID NO: 11". Similarly, in the amino acid sequence of SEQ ID NO: 13, the positions 1 to 20 constitute of a signal sequence. Accordingly, in the present specification, the wording "light chain consisting of the amino acid sequence of SEQ ID NO: 13" may be interchangeably read as "a light chain consisting of the amino acid sequence at positions 21 to 238 in the amino acid sequence of SEQ ID NO: 9".

A DNA sequence encoding the 1C10 antibody includes, for example, the nucleotide sequence (heavy chain) of SEQ ID NO: 6 and the nucleotide sequence (light chain) of SEQ ID NO: 8. As described above, in the nucleotide sequence (heavy chain) of SEQ ID NO: 6, 57 bases encode a signal sequence. Accordingly, in the present specification, the wording "nucleotide sequence of SEQ ID NO; 6" may be interchangeably read as "nucleotide sequence at positions 58 to 1425 in the nucleotide sequence of SEQ ID NO: 6". Similarly, in the nucleotide sequence (light chain) of SEQ ID NO: 8, 60 bases encode a signal sequence. Accordingly, in the present specification, the wording "nucleotide sequence of SEQ ID NO: 8" may be appropriately interchangeably read as "nucleotide sequence at positions 61 to 717 in the nucleotide sequence of SEQ ID NO: 8". Also, a DNA sequence encoding the 1D9 antibody includes, for example, the nucleotide sequence (heavy chain) of SEQ ID NO: 10 and the nucleotide sequence (light chain) of SEQ ID NO: 12. As described above, in the nucleotide sequence (heavy chain) of SEQ ID NO: 10, 57 bases encode a signal sequence. Accordingly, in the present specification, the wording "nucleotide sequence of SEQ ID NO: 10" may be appropriately interchangeably read as "nucleotide sequence at position 58 to 1419 in the nucleotide sequence of SEQ ID NO: 10". Similarly, in the nucleotide sequence (light chain) of SEQ ID NO: 12, 60 bases encode a signal sequence. Accordingly, in the present specification, the wording "nucleotide sequence of SEQ ID NO: 12" may be appropriately interchangeably read as "nucleotide sequence at positions 61 to 717 in the nucleotide sequence of SEQ ID NO: 12".

In the present specification, the expression "hybridize under a stringent condition" means hybridizing under a hybridization condition ordinarily used by those skilled in the art. For example, whether to hybridize can be determined according to the method described in Molecular Cloning, a Laboratory Manual, Fourth Edition, Cold Spring Harbor Laboratory Press (2012). Current Protocols in Molecular Biology, Wiley Online Library, or the like. For example, the hybridization condition may be a condition where hybridization is carried out with 6×SSC (0.9 M NaCl, 0.09 M trisodium citrate) or 6×SSPE (3M NaCl, 0.2 M NaH$_2$PO$_4$, 20 mM EDTA-2Na, pH 7.4) at 42° C. and then washed with 0.5×SSC at 42° C.

In an embodiment, the present invention relates to a polynucleotide encoding an amino acid sequence having 80% or more identity with each of the amino acid sequence of SEQ ID NO: 7 and the amino acid sequence of SEQ ID NO: 9, or the amino acid sequence of SEQ ID NO: 11 and the amino acid sequence of SEQ ID NO: 13 (referred to as "the amino acid sequences of SEQ ID NO: 7 and the like" in this paragraph). The identity of the amino acid sequence means the proportion (%) of the number of the same type of amino acids in a range of the amino acid sequence to be compared in two types of proteins. The identity of the amino acid sequence can be determined by, for example, a publicly known program such as BLAST or FASTA. The above identity may be a higher identity than an identity of 80% or higher, for example, an identity of 85% or more, 90% or more, 95% or more, 98% or more, or 99% or more. Alternatively, the polynucleotide of the present invention may also be a polynucleotide encoding an amino acid sequence exhibiting a homology score of 200 or more with the amino acid sequence of SEQ ID NO: 7 and the like in Blast. The homology score can be obtained by aligning each of the amino acid sequences of SEQ ID NO: 7 and the like and the amino acid sequence of a candidate protein, then determining the score of each amino acid to be compared from a score matrix, and calculating the total score thereof as the homology score. The homology score can be determined by, for example a publicly known BLAST program. As the score matrix, BLOSUM62, PAM32, and the like have been known, and BLOSUM62 is preferable in the present specification.

The number of amino acids which are substituted, deleted, added, and/or inserted are not particularly limited as long as it is a number that does not affect the biological activity of the antibody, but can be, for example, 1 to 10, 1 to 5, 1 to 4, or 1 to 3. The substitution of the amino acid is preferably substitution between conservative amino acids (see, Molecular Biology of the Cell, Garland Science; 6th edition).

The term "silk gland-specific gene promoter" is a promoter of a gene which is expressed specifically in the silk glands of the silk-spinning insects. Examples of such a promoter include silk protein gene promoters such as a posterior silk gland-specific gene promoter and a middle silk gland-specific gene promoter. Specific examples include sericin gene promoters (sericin 1 gene promoter, sericin 2 gene promoter, and sericin 3 gene promoter) or fibroin gene promoters (fibroin heavy chain gene promoter, fibroin light chain gene promoter, and fibrohexamerin gene promoter). Preferably, the silk gland-specific gene promoter is a sericin 1 gene promoter, a sericin 2 gene promoter, and sericin 3 gene promoter, and includes an MSG promoter and a PSG promoter (WO 2017135452 A1). The expression "functionally linked to downstream of the promoter" means being linked in the manner where the gene can be expressed by activation of the promoter.

In another embodiment, the present invention relates to a plasmid vector containing the above expression cassette. The plasmid vector is not particularly limited as long as it is a vector that can be introduced into cells of silk-spinning insects and maintained. Examples thereof include a plasmid vector into which DNA type transposon piggyBac derived from *Trichoplusia ni* is incorporated (Tamura, T et al. Nature Biotechnology, 18: 81-84 (2000)). Examples of the vector include pPIGA3GFP (Tamura, T et al., Nature Biotechnology, 18: 81-84 (2000)) and pBac [3xP3-DsRed/pA] (Nature Biotechnology, 21: 52-56 (2003)). The vector of the present invention can also be produced by, for example, inserting the above expression cassette into a cleavage site for the restriction enzyme of a vector (pMSG1.IMG) produced by the method described in US patent application publication No. 2008/0301823. Alternatively, the vector may also be a vector for silk-spinning insect transformation, pMSG3.IMG (Japanese Unexamined Patent Application Publication No. 2012-182995), for example.

In an embodiment, the present invention relates to a transgenic silk-spinning insect wherein the above expression cassette is incorporated into a chromosome thereof. In the present specification, the "silk-spinning insect" is not particularly limited as long as it is an insect that has silk glands and can spin silk threads. The "silk-spinning insect" means a Lepidoptera insect, a Hymenoptera insect, a *Neuroptera* insect, a *Trichoptera* insect, and the like that spin threads for nesting, cocooning, or moving mainly at the larva stage. The silk-spinning insect is preferably a Lepidoptera insect which can spin a large amount of silk threads, and specific examples thereof include species belonging to Bombycidae, Saturniidae, Brahmaeidae, Eupterotidae, Lasiocampidae, Psychidae, Arctiidae, Noctuidae, and the like. The silk-spinning insect includes a silkworm, *Bombyx* mandarina, *Samia cynthia, Samia cynthia ricini, Antheraea yamamai, Antheraea pernyi, Saturnia jonasii,* and *Actias artemis.* The transgenic silk-spinning insect of the present invention produces (secretes) the above antibody in silk threads (cocoon) (preferably, a sericin layer).

In another embodiment, the present invention relates to an antibody produced by the transgenic silk-spinning insect. The antibody may include an antibody including a heavy chain having the amino acid sequence of SEQ ID NO: 7 and/or a light chain having the amino acid sequence of SEQ ID NO: 9, or may include a heavy chain having the amino acid sequence of SEQ ID NO: 11 and/or a light chain having the amino acid sequence of SEQ ID NO: 13. The antibody may also include a heavy chain and/or a light chain comprising an amino acid sequence having 80% or more identity with the amino acid sequence of SEQ ID NO: 7 and/or SEQ ID NO: 9, respectively, or the amino acid sequence of SEQ ID NO: 11 and/or SEQ ID NO: 13, respectively. The antibody of the present invention may also have a heavy chain and/or a light chain comprising an amino acid sequence exhibiting a homology score of 200 or more with the amino acid sequence of SEQ ID NO: 7 and/or SEQ ID NO: 9, respectively, or the amino acid sequence of SEQ ID NO: 11 and/or SEQ ID NO: 13, respectively, in Blast. The antibody of the present invention may also have a heavy chain and a light chain consisting of amino acid sequences in which several amino acids are substituted, deleted, added, and/or inserted in SEQ ID NO: 7 and SEQ ID NO: 9, respectively, or SEQ ID NO: 11 and SEQ ID NO: 13, respectively. Further, in the present specification, the term "antibody" may be a part or a fragment of an antibody, or a modified antibody as long as it includes Fc and an antigen binding site. For example, the antibody may be a single-chain antibody (for example, a heavy chain antibody) or a bispecific antibody.

It is known that no fucose is bound as glycans in the antibody produced in the cocoon of silkworms. Also, an antibody to which fucose is not attached has been widely known to have excellent ADCC activity in the technical field. There has been no report on relationship between virus suppression by administration of the antibody and the ADCC activity so far. However, such an effect of the present invention may be brought by the ADCC activity. Accordingly, in an embodiment, the present invention may include an anti-HIV antibody composition containing an IgG antibody having a heavy chain comprising the amino acid sequence of SEQ ID NO: 7, an amino acid sequence having 80% or more identity with the amino acid sequence of SEQ ID NO: 7, or an amino acid sequence in which several amino acids are substituted, deleted, added, and/or inserted in the amino acid sequence of SEQ ID NO: 7, and a light chain comprising the amino acid sequence of SEQ ID NO: 9, an amino acid sequence having 80% or more identity with the amino acid sequence of SEQ ID NO: 9, or an amino acid sequence in which several amino acids are substituted, deleted, added, and/or inserted in the amino acid sequence of SEQ ID NO: 9; having a binding ability to HIV; and having the Fc region modified for improving ADCC activity, wherein the ADCC activity is higher than wild-type antibodies produced in CHO cells; and wherein the composition has an activity of suppressing HIV in the blood of an HIV-infected patient under detection limit at a probability of 90% or more with one or several times of administration to the HIV-infected patient.

Further, it has been indicated that the relationship between Fc and FcγR affects the ADCC activity, and it has been reported that the affinity with FcγR can be increased by amino acid substitution in the Fc region. In particular, a Fc which strongly binds to an activated form of FcγR such as FcγRIIIa, but weakly binds to an inhibitory FcγR such as FcγRIIb has been known to have excellent effector function. As such mutations, F158V, A330L, S239D, and 1332E (Greg ALazar et al., PNAS (2006) 103(11): 4005-4010): and F243L, D270E, R292P, S298N, Y300L, V305I, A330V, and P396L (Cancer Res (2007) 67(18): 8882-8890) have been reported. The Fc region of the antibody of the present invention may have such mutations, and may have 1 to 10 mutations selected from A330L, S239D, 1332E, F243L, D270E, R292P, S298N, Y300L, V305I, A330V, and P396L, for example.

In another embodiment, the present invention relates to a composition containing IgG antibodies having a binding ability to HIV, wherein 80% or more of the IgG antibodies does not have fucose in glycans binding to the antibody. In other words, in the composition of the present invention, it is not necessary that fucose is not included in the all anti-HIV antibodies (100%), and fucose may not include in at least 80% or more (preferably, 85% or more, 90% or more, 95% or more, 96% or more, 97% or more, 98% or more, and 99% or more) of the anti-HIV antibody. Preferably, the composition has an activity of suppressing HIV load in the blood of an HIV-infected patient below detection limit at a probability of 90% or more by one or several times of administration to the HIV-infected patient. The characteristics of the sequence and the like of the anti-HIV antibody contained in the composition are the same as those of the anti-HIV antibody of the present invention.

In the present specification, whether "an antibody has an activity of suppressing HIV load in the blood of an HIV-infected patient below detection limit at a probability of 90% or more (preferably, 92% or more, 93% or more, 94% or more, 95% or more, 96% or more, 97% or more, 98% or more, 99% or more, or 100%) by one or several times of administration to the HIV-infected patient" can be confirmed by administering an test antibody to a plurality of HIV-infected patients, and then detecting HIV in the blood thereof in accordance with an ordinary method, for example, a method utilizing PCR. When HIV in the blood is not detected in 90% or more of the HIV-infected patients to which the test antibody has been administered, it can be determined to have an activity of suppressing HIV in the blood of an HIV-infected patient below detection limit at a probability of 90% or more by one or several times of administration to the HIV-infected patient. The determination whether the antibody suppresses HIV load in the blood below detection limit is desirably conducted at a time after all of the administrations of the antibody have been completed. The determination is conducted preferably, at 12 weeks, 16 weeks, 20 weeks, 24 weeks, 28 weeks, 32 weeks, 36 weeks, 40 weeks, 1 year, 2 years, 3 years, 4 years, or 5 years after completion of administration.

Further, in another embodiment, the present invention relates to a therapeutic agent or a prophylactic agent (pharmaceutical composition) for HIV infection, containing the above antibody as an active ingredient. The pharmaceutical composition of the present invention may be in any formulation for oral or parenteral administration as long as it is a formulation that can be administered to a patient. Examples of the composition for parenteral administration include an injection, a nasal drop, a suppository, a patch, and an ointment. The composition is preferably an injection. The dosage form of the pharmaceutical composition of the present invention include a liquid formulation, or a lyophilized formulation. When the pharmaceutical composition of the present invention is used as an injection, excipients can be added as necessary that include a solubilizing agent such as propylene glycol and ethylenediamine: a buffer such as phosphate: a tonicity agent such as sodium chloride and glycerin; a stabilizer such as sulfite; a preservative such as phenol; and a soothing agent such as lidocaine (see "Japanese Pharmaceutical Excipients" Yakuji Nippo Limited. "Handbook of Pharmaceutical Excipients Fifth Edition" APhA Publications). When the pharmaceutical composition of the present invention is used as an injection, a storage container therefor may be an ampoule, a vial, a prefilled syringe, a cartridge for pen type syringes, a bag for infusion, and the like.

10

Advantageous Effects of Invention

The antibody of the present invention can be produced in silkworms with high efficiency, and therefore a therapeutic antibody for HIV infection with lower production cost can be provided.

BRIEF DESCRIPTION OF THE DRAWINGS

FIG. 4 shows the result of estimating the glycan structure of an antibody expressed in a cocoon of the silkworm and the glycan structure of an antibody produced in CHO cells from the mass spectrum. The main glycan structures and the abundances thereof are shown.

FIG. 6 is a graph showing the result when SW-1C10 is administered to a cynomolgus monkey inoculated with strong toxic SHIV89.6P (Reimann K. A. et al., J. Virol. 70, 6922-6928) in order to evaluate the effect of SW-1C10 in an acute infection phase. The left graphs show the results for a group to which SW-1C10 is administered (n=3), and the right graphs show the results for an untreated group (n=2). The vertical axis of the upper graph represents the number of copies of viral RNA in 1 ml of plasma ($\log_{10}$ copies/mL), and the vertical axis of the lower graph represents the number of CD4+T cells (count/μL). The systemic infection was established. The horizontal axis of all the graphs represents the time lapse (week) after viral infection. Administration of SW-1C10 was performed via vein on Day 3, Day 10, and Day 17 after virus inoculation.

MODE FOR CARRYING OUT THE INVENTION

1. Antibody

Figure 1:
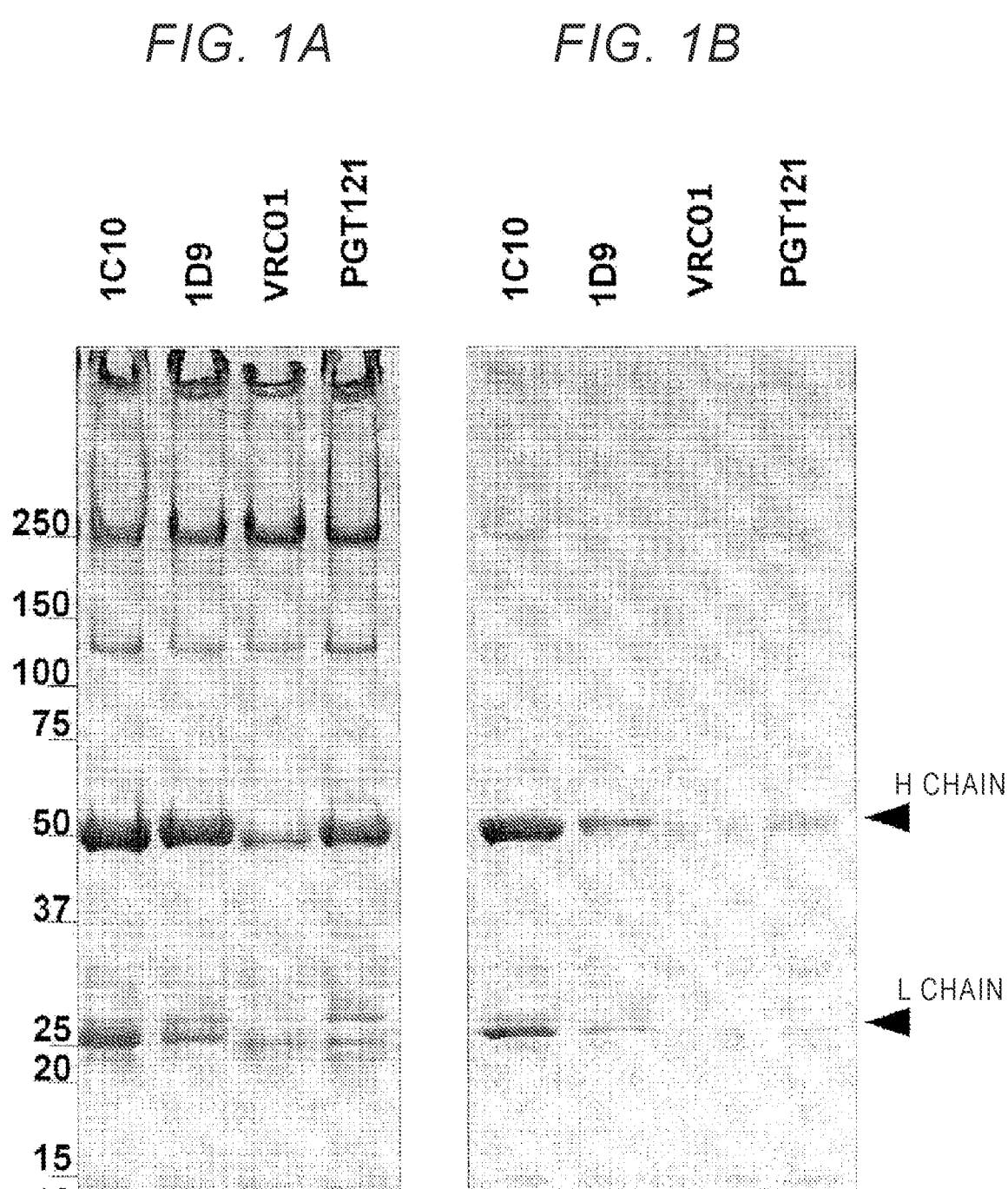
FIG. 1 is a photograph showing comparison for the expression level in a transgenic silkworm by CBB staining after SDS-PAGE. A: total proteins; B: neutral pH buffer extract. The numerical value on the left side of the photograph represents the molecular weight (kDa), and the upper part of the photograph represents the type of antibody used.

In an embodiment, the present invention includes a method for producing the antibody of the present invention, including expressing the antibody gene of the present invention in silkworms, as well as an antibody produced by the method. The production method of the present invention can be specifically performed by the following method.

Production of Expression Cassette

The expression cassette of the present invention containing an antibody gene functionally linked to a promoter region causing gene expression in silk gland cells in the silkworm can be produced by binding a polynucleotide encoding a promoter region causing gene expression in silk gland cells in the silkworm to any one polynucleotide selected from the above (i) to (x) utilizing a gene recombination technology known to those skilled in the art. The polynucleotide of a promoter region causing gene expression in silk gland cells in the silkworm can be obtained by, for example, performing PCR using a genomic DNA extracted from silkworm cells as a template and using a promoter corresponding to a desired promoter. For example, US patent application publication No. 2008/0301823 describes a method for acquiring a sericin 1 gene promoter.

When the expression cassette of the present invention includes an enhancer, a polynucleotide encoding a −1860 to −1127 region and/or a −5000 to −3848 region of fibroin heavy chain gene, a polynucleotide encoding the baculovirus homologous region, a polynucleotide constituting the 5' untranslated region of baculovirus polyhedrin, and/or a polynucleotide encoding baculovirus IE1, and the like, the expression cassette can be obtained by binding these polynucleotides to an antibody gene functionally linked to a promoter region causing gene expression in silk gland cells of silkworms, in accordance with a method known to those skilled in the art (for example, by utilizing a cleavage site for the restriction enzyme). For example, the expression cassette of the present invention can be produced in accordance with the methods described in Japanese patent application publication No. 2004-344123, US patent application publication No. 2008/0301823, Japanese patent application publication No. 2008-125366, and the like.

Production of Vector

A plasmid vector containing the above expression cassette can be obtained by incorporating the above expression cassette or its constituent into a desired vector. The vector is not particularly limited as long as it is a plasmid vector that can produce a transgenic silkworm. The vector can be produced by, for example, inserting the above expression cassette into a cleavage site for the restriction enzyme of the above vector.

Production of Transgenic Silkworm

In an embodiment, the present invention relates to a method for producing a transgenic silkworm which produces (secretes) the antibody in silk threads (cocoon) (preferably, in a sericin layer) comprising, inserting the above plasmid vector into eggs of a silk-spinning insect. Specifically, the method for producing the transgenic silkworm of the present invention includes injecting the plasmid vector into silkworm eggs (silkworm embryos) 2 to 8 hours after egg laying, interbreeding hatched silkworm imagoes to obtain G1 egg masses, and screening transgenic silkworms into which the expression cassette of the present invention is incorporated by using expression of a marker gene and the like as an indicator.

As an example, after purification of the obtained plasmid, the plasmid is mixed with a helper plasmid pHA3PIG (Nat. Biotechnol. 18, 81-84 (2000)) in the amount ratio of 1:1, which is subjected to ethanol precipitation and dissolved in an injection buffer (0.5 mM phosphate buffer: pH 7.0, 5 mM KCl) so that the DNA concentration is 10 to 1,000 µg/ml. This vector mixed solution is injected into silkworm eggs (silkworm embryos) at 2 to 8 hours after egg laying at the pre-blastoderm stage in a trace liquid amount of about 1 to 200 nl per egg. The eggs injected by the trace amount of vector DNA are incubated at about 25° C., and the hatched silkworms are reared. The obtained fertile imagoes are interbred to obtain broods of eggs at G1 generation. Eggs of a transgenic silkworm emitting green fluorescence from the eyes and the nervous system thereof are selected from the G1 egg broods on Day 3 to Day 10 from the day of egg laying, and then hatched, thereby establishing a transgenic silkworm into which antibody cDNA is incorporated.

Further, in the transgenic silkworm of the present invention, a polynucleotide for enhancing the gene expression may be introduced separately from the expression cassette of the present invention. For example, a polynucleotide for enhancing gene expression may be inserted into a plasmid vector different from the plasmid vector of the present invention, and injected into silkworm eggs at the same time with or separately from the plasmid vector of the present invention. Alternatively, a transgenic silkworm introduced with the expression cassette of the present invention and the polynucleotide for enhancing gene expression can be obtained by interbreeding a transgenic silkworm into which the expression cassette of the present invention has been introduced by the above method with a transgenic silkworm introduced with a polynucleotide for enhancing gene expression. For example, the above obtained transgenic silkworm can be interbred with a silkworm expressing the ie1 gene which is a trans-activator derived from BmNPV (Japanese patent application publication 2012-182995), and then silkworms having both the antibody cDNA and the ie1 gene can be selected from the obtained G2 generation silkworms.

Production Method of Antibody

In another embodiment, the present invention relates to a method for producing an antibody comprising a heavy chain having the amino acid sequence of SEQ ID NO: 7 and a light chain having the amino acid sequence of SEQ ID NO: 9, or an antibody comprising a heavy chain having the amino acid sequence of SEQ ID NO: 11 and a light chain having the amino acid sequence of SEQ ID NO: 13, comprising extracting the antibody from silk threads produced from the transgenic silk-spinning insect.

For example, in the production of the antibody, the above silkworms are reared to spin cocoons. The cocoons of the silkworms are immersed in an extraction buffer (PBS (final concentration of NaCl: 0.5 M), and 0.1% Triton X-100) and stirred at room temperature for 1 hour to prepare a cocoon extract. The extract is filtrated with a 0.45-µm filter, and loaded to a protein G column (Protein G Sepharose 4 Fast Flow, GE Healthcare). The elute obtained with 0.1 M glycine (pH 2.7) is neutralized by adding 1 M Tris-HCl (pH 9.0), and then finally dialyzed against PBS, which would give the antibody.

Also, a fragment of the antibody can be prepared by various methods known to those skilled in the art. The fragment can be obtained by, for example, subjecting the antibody obtained by the above method to papain treatment.

In addition to the above method of producing an antibody in the cocoon of silkworms, the preparation methods of antibody without fucose binding are known such as a method of producing an antibody by cells exhibiting reduced fucosylation which are selected by killing cells having high fucose in CHO cells treated with an agent (US patent application publication No. 2010/0081150), a method of producing an antibody by using CHO cell lines in which fucosylation is reduced due to spontaneous mutation in Fx protein and control of fucose supply from the outer source (US patent application publication No. 2010/0304436), a method of producing an antibody by using GMD knockout cells in which genome corresponding to GMD exon 5, 6 and 7 regions are deleted and FUT8 knockout host cell lines (KANDA, Y. et al. (2007) J. BIOTECHNOL; 130(3): 300-10), a method of producing an antibody by using four types of lectin-resistant CHO mutant cells which have been obtained by being incubated with N-methyl-N-nitrosogua-nidine (RIPKA, J. et al. (1986) SOMAT CELL MOL GENET; 12(1): 51-62), a method of producing an antibody by using Lec13 (fucose-deficient CHO) cell lines (SHIELDS, R. L. et al. (2002) J BIOL CHEM; 277(30): 26733-40), a method of producing an antibody by using CHO cells which have been obtained by contacting a population of methotrexate (MTX) treated CHO cells with a non-toxic fucose binder of *Aleuria aurantia* lectin (AAL) or *Aspergillus oryzae* 1-fucose-specific lectin (AOL) to remove cells bound to the fucose binder (WO2012/120500), a method of cleaving the glycan from the antibody, and then attaching a non-fucose containing glycan to the antibody (Japanese patent application publication 2016-082962), and a method of producing an antibody by using cells expressing acetylglucosaminyltransferase III (U.S. Pat. No. 6,602,684). The antibody of the present invention may be produced by any of these methods, or other publicly known antibody production methods not described herein, in which the amount of fucose bound is reduced.

2. Pharmaceutical Composition

The antibody of the present invention can be used as a pharmaceutical composition in the form of oral administration, or in the form of parenteral administration such as an injection or a drip infusion. When the pharmaceutical composition is administered to mammals and the like, the pharmaceutical composition can be in the form of oral administration such as a tablet, a powder, a granule, or a syrup, or can be in the form of parenteral administration such as an injection or a drip infusion.

The pharmaceutical composition of the present invention can be formulated by using a normal pharmaceutically acceptable carrier by an ordinary method. In preparing a solid formulation for oral administration, an excipient, further, as necessary, a binder, a disintegrant, a lubricant, and the like are added to the base, and then this is formulated into a solution, a granule, a powder, a capsule, and the like by an ordinary method. In preparing an injection, a pH adjusting agent, a buffer, a stabilizer, a solubilizer, and the like are added to the base as necessary, and this can be used as an injection for subcutaneous or intravenous administration by an ordinary method.

In another embodiment, the present invention relates to a method for treatment or prevention of HIV infectious disease, comprising administering an effective amount of the antibody of the present invention to a patient in need thereof. Alternatively, the present invention relates to a use of the antibody of the present invention for manufacturing a therapeutic composition or a prophylactic composition for HIV infection. The dose when the antibody of the present invention is administered to mammals and the like varies depending on symptom, age, gender, body weight, and type of administration form. When the antibody of the present invention is intravenously administered to an adult, for example, the dose per administration can be usually 0.1 to 10,000 mg. The administration method is preferably a method that can maintain HIV load in the blood at the detection limit or lower over a long period of time after administration (for example, 12 weeks or more, 16 weeks or more, 20 weeks or more, 24 weeks or more, 28 weeks or more, 32 weeks or more, 36 weeks or more, 40 weeks or more, 1 year or more, 2 years or more, 3 years or more, 4 years or more, or 5 years or more). In order to check whether HIV load in the blood is maintained at the detection limit or lower after administration, the amount of HIV load in the blood (for example, HIV RNA amount) may be monitored as necessary during or after the administration period. The antibody of the present invention can be administered to a patient infected with HIV, for example, 1 to 10 times, 1 to 8 times, 1 to 5 times, 1 to 4 times, 1 to 3 times, 1 to 2 times, 1 time, 2 times, or 3 times in total. The administration interval can be 3 to 30 days, 3 to 15 days, 4 to 10 days, 5 to 9 days, 6 to 8 days, or 7 days.

Although the present invention will be hereinafter described in detail with reference to examples, the present invention is not intended to be limited thereto. All documents cited throughout the present specification are incorporated as it is into the present specification by reference. The present application claims the priority based on Japanese Patent Application No. 2018-203114 filed on Oct. 29, 2018. The entire contents of Japanese Patent Application No. 2018-203114 to which the present application claims the priority are incorporated herein by reference.

EXAMPLES

(1) Production of Vector cDNA of a 1C10 heavy chain was amplified by performing PCR using, as a template, a plasmid (pMPE-1C10) into which cDNAs of a heavy chain (SEQ ID NO: 6) and a light chain (SEQ ID NO: 8) of the 1C10 antibody are incorporated; as a forward primer, a mixed solution of a primer containing a restriction enzyme NruI recognized sequence and the 5' untranslated region sequence of BmNPV polyhedrin (NruI-BmNPV-ATG) (Japanese Unexamined Patent Application Publication No. 2008-125366) and a primer (Hc-F) consisting of a sequence of the 5' end of the 1C10 heavy chain; and as a reverse primer, a primer consisting of a sequence of the 3' end of the heavy chain and restriction enzyme NruI and XhoI recognized sequences (C-hIgG1-NruI-XhoI).

The amplified fragments were treated with XhoI, and incorporated into a cloning vector (pCR-MCS) treated with EcoRV and XhoI. Similarly, cDNA of a 1C10 light chain was amplified by performing PCR using, as a template, a plasmid (pKVA2-1C10) into which cDNA of the 1C10 light chain is incorporated; as a forward primer, a mixed solution of NruI-BmNPV-ATG and a primer (LcK-F) consisting of a sequence of the 5' end of the light chain; and as a reverse primer, a primer (LcK-R) consisting of a sequence of the 3' end of the light chain and restriction enzyme NruI and XhoI recognized sequences, and then the obtained fragments are inserted into the pCR-MCS.

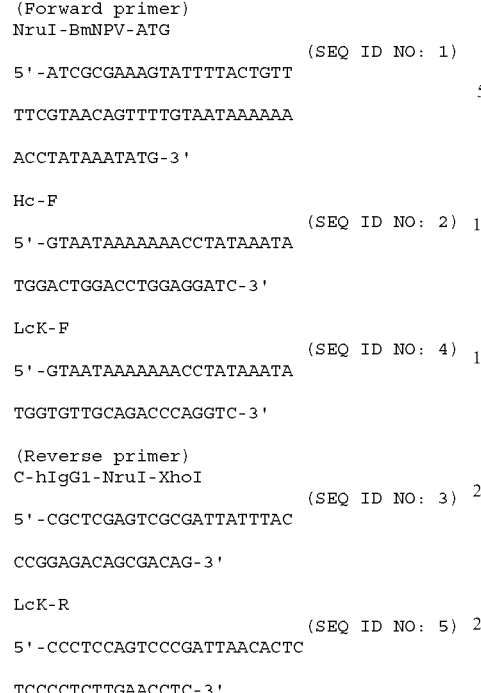

(Forward primer)
NruI-BmNPV-ATG (SEQ ID NO: 1)

5'-ATCGCGAAAGTATTTTACTGTT

TTCGTAACAGTTTTGTAATAAAAAA

ACCTATAAATATG-3'

Hc-F (SEQ ID NO: 2)

5'-GTAATAAAAAAACCTATAAATA

TGGACTGGACCTGGAGGATC-3'

LcK-F (SEQ ID NO: 4)

5'-GTAATAAAAAAACCTATAAATA

TGGTGTTGCAGACCCAGGTC-3'

(Reverse primer)
C-hIgG1-NruI-XhoI (SEQ ID NO: 3)

5'-CGCTCGAGTCGCGATTATTTAC

CCGGAGACAGCGACAG-3'

LcK-R (SEQ ID NO: 5)

5'-CCCTCCAGTCCCGATTAACACTC

TCCCCTCTTGAACCTC-3'

The pCR-MCS into which the cDNA of the 1C10 light chain has been incorporated was cut with NruI to cut out the cDNA of the light chain. Then, the cut cDNA of the light chain was incorporated into a vector for producing transgenic silkworms treated with Aor51HI (pMSG3.1MG, Japanese Unexamined Patent Application Publication No. 2012-182995). Next, this vector was digested with NruI, and ligated to the cDNA of the heavy chain cut out with NruI from the pCR-MCS into which the cDNA of the 1C10 heavy chain has been incorporated. In the obtained vector (1C10/pMSG3.1MG), the cDNAs of 1C10 heavy chain and light chain were each incorporated downstream of the sericin 1 promoter.

Vectors for producing a transgenic silkworm, wherein the heavy chain and the light chain of 1D9 (cDNA sequence of the heavy chain: SEQ ID NO: 10; cDNA sequence of the light chain: SEQ ID NO: 12) and 49G2 which are anti-HIV human antibodies derived from the same patient as 1C10 as well as VRC01 (Science. 329, 856-61 (2010)) and PGT121 (Nature. 477, 466-470 (2011)) which are human antibodies derived from another HIV patient, were incorporated into the pMSG3.1MG, were prepared by the same method.

(2) Preparation of Transgenic Silkworm

The 1C10/pMSG3.IMG was purified with Plasmid Midi Kit (QIAGEN), and then mixed with pHA3PIG (Nat. Biotechnol.; 18: 81-84 (2000)) as a helper plasmid so that the amount ratio of plasmid was 1:1. The mixture was subjected to ethanol precipitation and dissolved in an injection buffer (0.5 mM phosphate buffer: pH 7.0, 5 mM KCl) so that the DNA concentration was 200 μg/mL. This vector mixed solution was micro-injected into 383 silkworm eggs (silkworm embryos) 2 to 8 hours after egg laying at the preblastoderm stage in a liquid amount of about 15 to 20 nl per egg.

The eggs, into which a vector DNA was micro-injected, were incubated at 25° C. and 85% of the eggs were hatched. These silkworm larvae were reared, the grown imagoes were interbred, and G1 generation eggs of 72 broods (egg masses laid by female imagoes) were thus obtained. The G1 egg masses on Day 5 to Day 6 from the day of egg laying were observed with a fluorescence stereoscopic microscope, and 31 broods of egg containing eggs of the transgenic silkworm emitting green fluorescence from the eyes and the nervous system thereof were obtained. The obtained eggs were hatched and reared to establish 48 transgenic silkworms. The cocoon protein of each of these silkworms was extracted and analyzed by SDS-PAGE. Further, genomic DNA was extracted from each of the imagoes, and Southern blotting was performed. Based on these analyses, 6 lines of transgenic silkworms in which the 1C10 antibody was expressed in the cocoon thereof, and which have a single copy of recombinant gene in their genomes were selected.

The above transgenic silkworms were interbred with silkworms expressing the ie1 gene which is a trans-activator derived from BmNPV (Japanese Unexamined Patent Application Publication No. 2012-182995). The IE1 protein synthesized from the ie1 gene is known to act on the hr3 enhancer derived from BmNPV included in the pMSG3.1MG and the sericin 1 promoter to increase the expression level of the recombinant protein in the middle silk gland (Biotechol. Bioeng.; 106:860-870 (2010)). Silkworms having both 1C10 cDNA and ie1 gene (hereinafter, denoted as "1C10 production line") were selected from the interbred G2 generation silkworms, and these silkworms were reared to spin cocoons.

Similarly, a vector, into which cDNA of each of 1D9 and 49G2 derived from the same patient as that of 1C10, or each of VRC01 and PGT121 derived from another patient has been incorporated, was micro-injected into silkworm eggs to produce each transgenic silkworm. The produced transgenic silkworm was interbred with the silkworm expressing the ie1 gene, and the interbred silkworm was caused to spin a cocoon containing each antibody.

The weight of the cocoon layer of the obtained cocoon for each one line of silkworm into which each gene was incorporated was shown (Table 1). As for 1C10, 1D9, VRC01, and PGT121, a cocoon with an average weight was formed, but no cocoon was formed as for 49G2.

TABLE 1

|  | 1C10 | 1D9 | 49G2 | VRC01 | PGT121 |
|---|---|---|---|---|---|
| Average cocoon weight (mg) | 65.0 | 91.1 | No cocoon was formed | 84.7 | 74.4 |
| Amount of antibody extracted from 1 mg of cocoon (μg) | 22.7 | 5.0 | — | 1.4 | 2.9 |
| Amount of antibody extracted from one cocoon (mg) | 1.48 | 0.46 | — | 0.12 | 0.22 |

(3) Analysis of Expression Level

The expression level of the antibody for each of 1C10, 1D9, VRC01, and PGT121, in which the cocoon was obtained, was examined. 10 mg of cocoon of each silkworm was immersed in 1 mL of 8 M urea, 50 mM Tris buffer (pH 8.0), and 0.1 M DTT, and then heated at 80° C. for 5 minutes to solubilize all the protein contained in the sericin layer of the silk threads (total proteins). Then, SDS-PAGE was performed under the reduced conditions, followed by CBB staining, and the expression levels of the antibodies were compared.

The results are shown in FIG. 1A. The heavy chain (H chain) and the light chain (L chain) of the antibody were detected from each of cocoons of the four types of transgenic silkworms. The expression level was the highest in 1C10, and relatively high in 1D9 and PGT121. However, the expression level was lower in VRC01 than the former antibodies.

Next, the amount of extracted antibody in a neutral pH buffered solution was analyzed. 10 mg of cocoon was immersed in 1 mL of PBS (final concentration of NaCl: 0.5 M) containing 0.1% Triton X-100, and then stirred at room temperature for 1 hour, followed by centrifugation, to recover the supernatant. When the protein in the extract was analyzed by SDS-PAGE, the amount of extracted antibody was the largest in 1C10, and the extraction ratios of 1D9 and PGT121, which were relatively high in the expression level, were considerably lower than that of 1C10. The amount of antibody contained in the extract was determined by using an HPLC system (Alliance HPLC System, Waters) equipped with a protein A column (HiTrap MabSelect SuRe column ($0.7 \times 2.5$ cm: 1 mL). GE Healthcare). 300 μL of extract prepared from each silkworm cocoon was applied to the protein A column, followed by washing with PBS. Thereafter, the bound antibody was eluted with 100 mM citric acid (pH 3.0). The concentration of the antibody was then determined from the area of the elution peak. Further, the amount of antibody extracted per cocoon was calculated from this result. Table 1 shows that the amount of antibody that can be extracted per cocoon of 1C10 was 1.48 mg, and an amount of antibody about 3.2 times the amount of 1D9 derived from the same HIV-infected patient can be extracted.

(4) Purification of 1C10 Antibody

The cocoon of the 1C10 production line was immersed in PBS (final concentration of NaCl: 0.5 M) containing 0.1% Triton X-100, and stirred at room temperature for 1 hour to prepare a cocoon extract. The extract was filtrated with a 0.45-μm filter, and applied to a protein G column (Protein G Sepharose 4 Fast Flow, GE Healthcare). A 0.1 M glycine-HCl buffer (pH 2.7) was used for elution of the antibody from the column. The eluted antibody solution was neutralized by adding 1 M Tris-HCl (pH 9.0) thereto, and the resulting solution was finally dialyzed against PBS. The purified antibody was used as SW-1C10 for the following experiments.

(5) Preparation of 1C10 Antibodies Derived from Different Origins

In order to examine the difference in the binding activity and neutralizing activity due to the origin of the antibody, 1C10 antibodies derived from different origins, namely, Bcell-1C10 (Virology.; 475: 187-203 (2015)), 293A-1C10 (Virology.; 475: 187-203 (2015)), and CHO-1C10 were prepared.

The CHO-AC10 was produced as follows. Transfection of a plasmid (pMPE-1C10) in which cDNA of 1C10 was incorporated into ExpiCHO-S cells (attached to a kit) was performed by using an ExpiCHO Expression System Kit (ThermoFisher Scientific). The culture supernatant was collected 12 to 14 days after transfection, then filtrated with a 0.2-μm filter, and allowed to be bound to a protein A column (HiTrap rProtein A FF, GE Healthcare). A 50 mM glycine-HCl buffer (pH 2.39) was used for elution of the antibody from the column. The eluted antibody solution was neutralized by adding 1 M Tris-HCl (pH 9.0) thereto, and the resulting solution was dialyzed against PBS. The antibody solution was concentrated by using PEG 6,000 (Wako), and then the solution was again dialyzed twice against PBS.

(6) Measurement of Binding Activity to HIV-A BaL Strain

Comparison of the binding activity to the HIV-1 BaL strain (Science.; 253: 71-4 (1991)) between SW-1C10 and 293A-1C10 was performed. First. BaL virus infected cells were prepared. A suspension of CEM.NKR-CCR5 (NKR24) cells (J Virol.; 86: 12039-52 (2012)) ($1 \times 10^6$ cells/50 μL) and 50 μL of suspension of the BaL virus cells were mixed in a 1.5-mL tube, and centrifuged at $1,200 \times g$ for 2 hours at room temperature. An R10 medium (J Virol.; 86: 12039-52 (2012)) was added thereto, and then culturing was started on a 24-well plate at 37° C. under 5% C02. A Luciferase gene controlled by an LTR promoter of HIV-1 is introduced into the NKR24 cells (J Virol.; 86: 12039-52 (2012)). The Luciferase activity produced in the NKR24 cells was measured by the neolite Reporter Gene Assay System (Perkin Elmer), and the state of virus infection was checked as appropriate.

FACS analysis samples were prepared at the stage in which BaL-infected NKR24 cells and noninfected (Normal) NKR24 cells were prepared (0.2% BSA/PBS was used as a reaction solution). 50 μL of suspension of cells prepared by suspending cells in the reaction solution at $2.5 \times 10^6$ cells/mL was added to a 96-well plate ($25 \times 10^4$ cells/tube). An equivalent amount of antibody solution (concentration was adjusted with D-PBS(–)) was added thereto at final concentrations of 0.032/0.16/0.8/4/20/100 μg/mL. The cells were incubated for 30 to 40 minutes at room temperature, and washed twice with a reaction solution. Then, 50 μL of APC-labeled anti-human IgG (Jackson ImmunoResearch) diluted 200 times with a reaction solution was added thereto (thereafter, operation was carried out with light shielding). The resulting cells were incubated for 15 minutes at room temperature, washed twice with a reaction solution, and then 100 μL of 10% Formalin/PBS was added thereto. The cells were incubated on ice for 15 minutes, and then analyzed by BD FACS Canto II (BD Biosciences). The binding activity was examined from the mean fluorescence intensity (MFI) of the APC.

Figure 2:
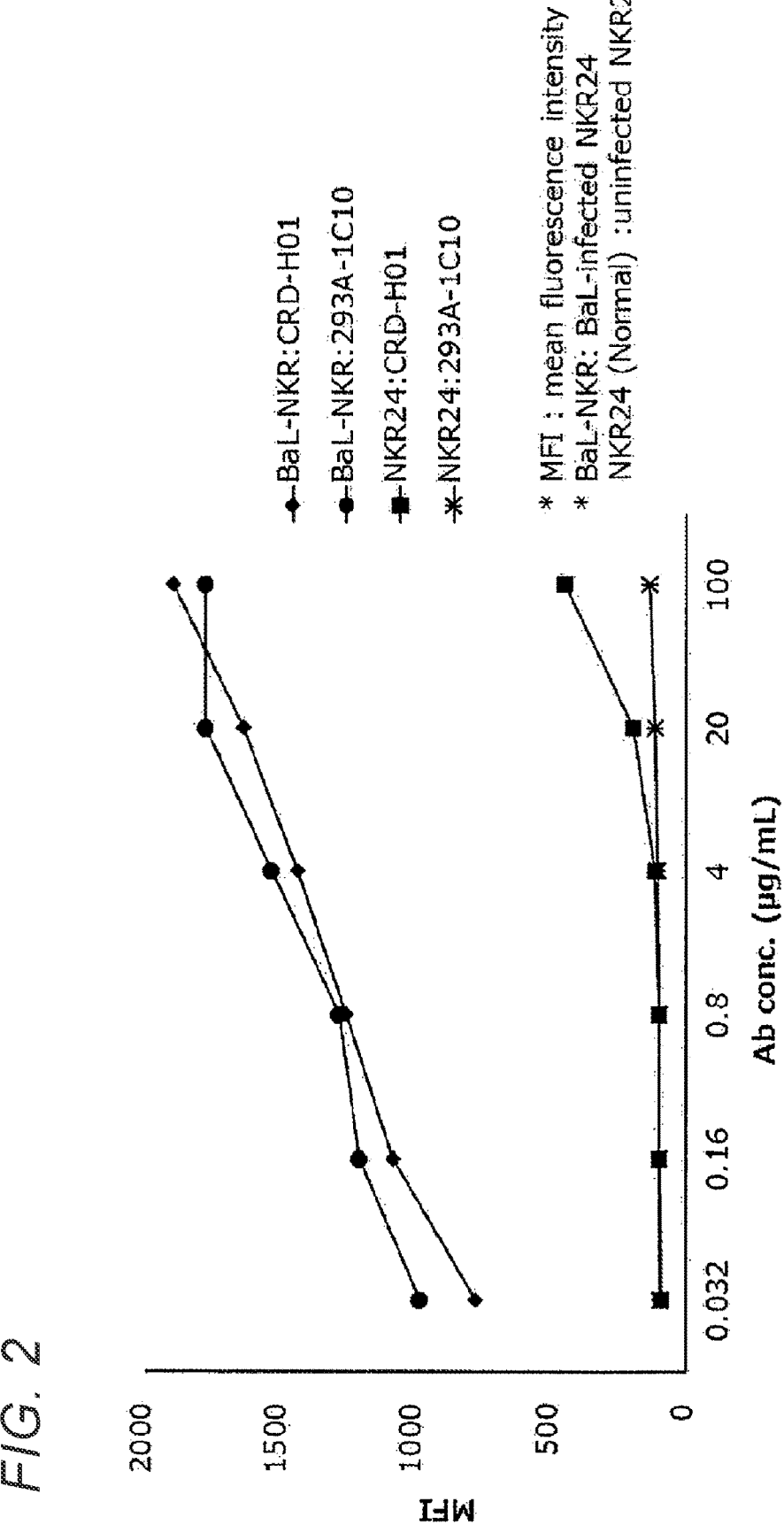
FIG. 2 is a graph showing the measurement result of the binding activity of each of antibodies produced in the transgenic silkworm to the HIV-1 BaL strain. The vertical axis represents the mean fluorescence intensity (MFI), and the horizontal axis represents the antibody concentration (μg/mL).

The results show that SW-1C10 and 293A-1C10 are both bound specifically to the BaL-infected NKR24 cells, and further, exhibit the binding activity dependent on the antibody concentration (Table 2 and FIG. 2).

TABLE 2

| Cells | Ab | Ab conc. (μg/mL) | | | | | |
|---|---|---|---|---|---|---|---|
| | | 0.32 | 0.16 | 0.8 | 4 | 20 | 100 |
| BaL-NKR24 | SW-1C10 | 779 | 1085 | 1261 | 1439 | 1640 | 1897 |
| | 293A-1C10 | 983 | 1212 | 1287 | 1533 | 1778 | 1781 |
| NKR24 | SW-1C10 | 91.2 | 100 | 100 | 114 | 198 | 451 |
| (Normal) | 293A-1C10 | 98.2 | 100 | 103 | 106 | 115 | 136 |

(7) Measurement of Neutralizing Activity to HIV-1 BaL Strain

Comparison of the neutralizing activity to the HIV-1 BaL strain among SW-1C10, Bcell-1C10, 293A-1C10, and CHO-1C10 was performed. 5-fold antibody dilution series in 8 stages with 4 μg/mL being a maximum concentration were prepared on a 96-well plate (100 μL/well). Then, 50 IL of BaL virus prepared to 4,000 TCID 50/mL was added thereto (final 200 TCID50). After incubation at 37° C. under 5% $CO_2$ for 1 hour, TZM-bl cells (AIDS; 23: 897-906 (2009)) were prepared to $1\times10^5$ cells/mL (+37.5 μg/mL DEAE dextran), and added thereto in an amount of 100 μL. Wells including a VC (virus control; only virus and cells) as a positive control, and a CC (cell control; only cells) as a negative control were prepared at the same time. After culturing at 37° C. under 5% $CO_2$ for 2 days, the cells were washed with PBS, and 30 μL of Luciferase Cell Lysis Buffer (Promega) was added to each well, followed by stirring for 15 minutes. 50 μL of Luciferase Assay Reagent was added to a white plate for detection (Coster), and then 10 μL of cell lysate after stirring was added thereto. The RLU (relative luminescence unit) was measured by a luminometer. The infection inhibition ratio (% inhibition)={(RLU in VC)-(RLU in each antibody concentration)}/(RLU in VC) was calculated as the RLU in CC being the background, and IC50 (50% inhibitory concentration) was determined.

Figure 3:
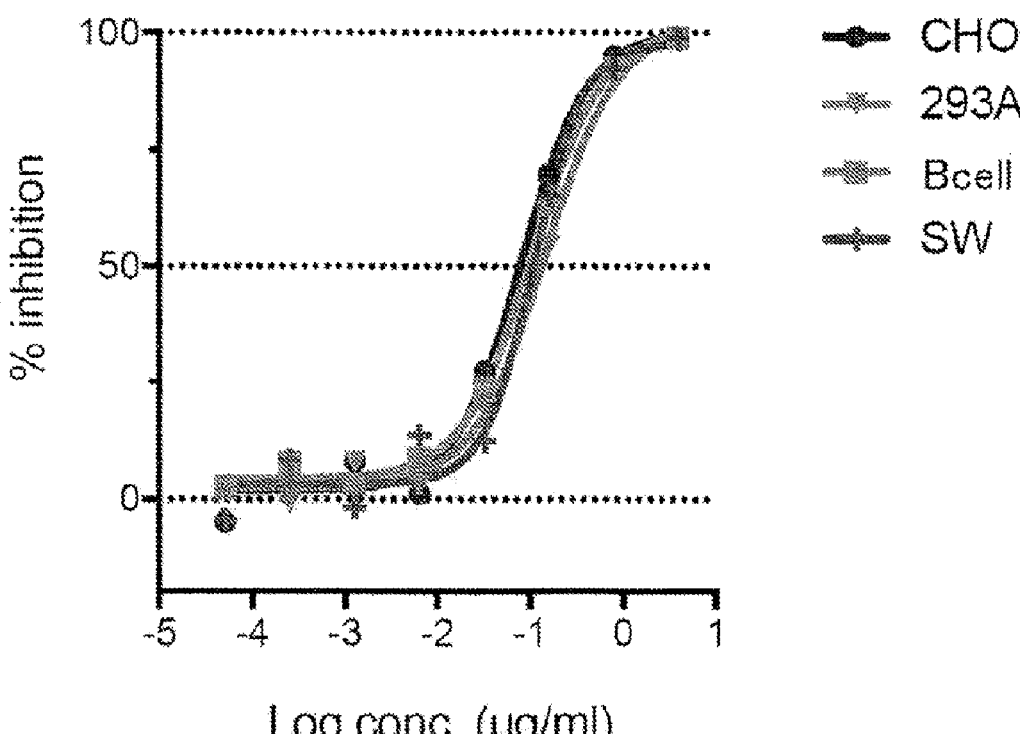
FIG. 3 is a graph showing the measurement result of the neutralizing activity of each of antibodies derived from different origins against the HIV-1 BaL strain. The vertical axis represents the inhibition percentage (% inhibition), and the horizontal axis represents the Log concentration of the antibody (μg/mL). The table below shows the inhibition percentage (% inhibition) in each concentration of each antibody.

Table 3 shows IC50, and FIG. 3 shows the infection inhibition ratio in each antibody concentration. The results show that various antibodies containing SW-1C10 exhibit approximately the same neutralizing activities.

TABLE 3

|  | SW | Bcell | 293A | CHO |
|---|---|---|---|---|
| Dose at Y = 50 | 0.1084 | 0.09697 | 0.1326 | 0.07808 |

(8) Analysis of Glycan Structure

The glycan structure of each of SW-1C10 and CHO-1C10 was analyzed in accordance with a literature (Mol. Cellular Proteom.; 6: 1437-1445 (2007)) by the following operation. 50 μg of each purified 1C10 was subjected to reductive alkylation and trypsin digestion in the presence of a surfactant, and then subjected to enzyme digestion with PNGaseA, thus releasing N-glycan. Subsequently, 50 pmol of internal standard substance was added, and the Glycoblotting method was performed (in this process, capturing of N-glycan, methylation of a carboxyl group, and BOA labeling were performed. This was subjected to mass analysis (MALDI-TOF-MS: Ultraflex III, positive mode). The obtained spectrum was compared with GlycoMod Tool to estimate the structure of N-glycan. Further, each peak area was normalized by using the peak area with the internal standard substance added in advance.

The principal glycan structures estimated from the obtained mass spectrum and the abundances thereof were shown in FIG. 4. About 70.3% of core fucose-added glycan was observed in CHO-1C10, whereas the core fucose-added glycan was not detected at all from SW-1C10. Further, the glycan of SW-1C10 was similar to the glycan structure of CHO-1C10 in that a glycan containing sialic acid addition or bisecting GlcNAc was not present.

(9) Measurement of ADCC Activity

KD-247, which is a humanized antibody recognizing the V3 loop of gp120, was prepared in addition to SW-1C10, 293A-1C10, and CHO-1C10. Comparison of the ADCC activity to the HIV-1 BaL strain was performed among these antibodies.

BaL-infected NKR24 cells were prepared by a method as in the case of binding activity measurement. Samples for ADCC activity measurement were prepared at the stage in which BaL-infected NKR24 cells and noninfected (Normal) NKR24 cells were prepared (R10 medium IOU/ml IL-2 was used as a reaction solution and an antibody diluent). 40 μL of NKR24 cells, which were washed three times with the reaction solution and prepared to $2.5\times10^5$ cells/mL, were added to a 96-well plate ($1\times10^4$ cells/well). 40 μL of human CD16+KHYG-1 cells being a natural killer cell line ((N6 cells; J Virol.; 86: 12039-52 (2012)), which were washed once with the reaction solution and prepared to $2.5\times10^6$ cells/mL, were added as the effector cell ($10\times10^4$ cells/well). Thereafter, 20 μL of each prepared antibody was added at a final concentration of 0.2, 2, or 20 μg/mL. Wells including a VC (virus control; only BaL-infected NKR24 cells and N6 cells) as a positive control, and a CC (cell control; only noninfected NKR24 cells and N6 cells) as a negative control were prepared at the same time, and incubation was performed at 37° C. under 5% $CO_2$ for 6 hours.

Figures 5A, 5B:
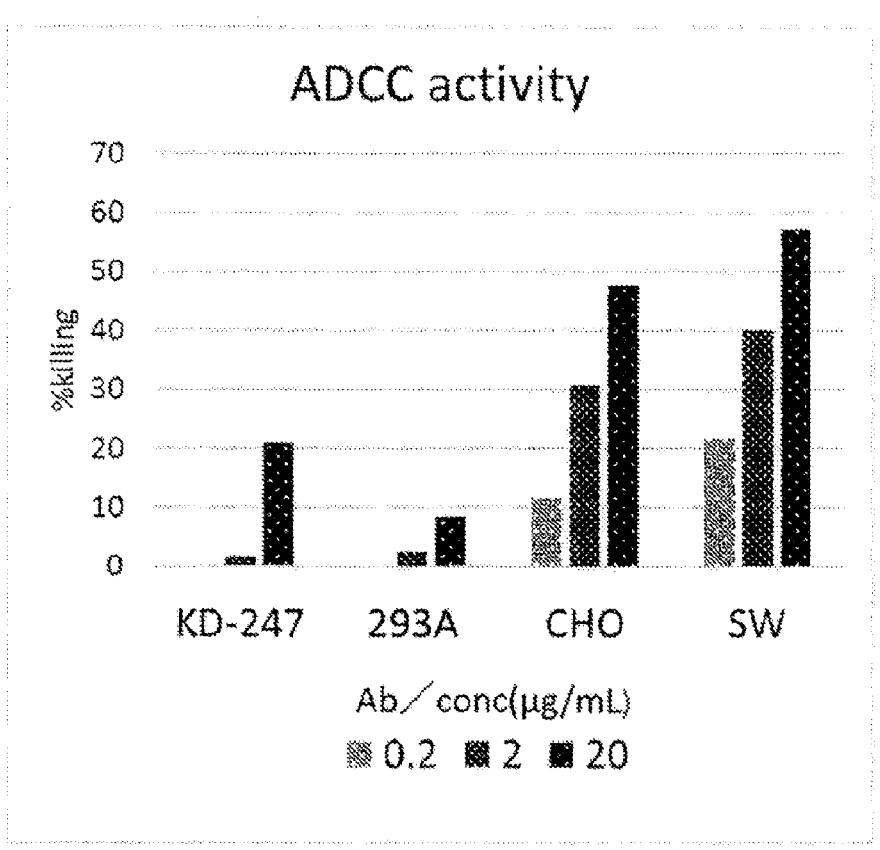
FIG. 5 shows a graph (A) and a table (B) each showing the measurement result of the ADCC activity when SW-1C10, 293A-1C10, CHO-1C10, and KD-247 (0.2, 2, 20 μg/mL) are each added to the HIV-1 BaL strain. The ADCC activity was the highest in SW-1C10, and the second highest in CHO-1C10.

A neolite Reporter Gene Assay System was used for ADCC activity measurement. 40 μL of neolite reagent was added to a white plate for detection (Perkin Elmer), then the reaction solution after incubation was suspended, and 40 μl of the suspension was added thereto. The RLU (relative luminescence unit) was measured by a luminometer. The virus killing ratio (% killing; (RLU in VC-RLU in each antibody concentration)/RLU in VC) was calculated as the RLU in CC being the background, and the calculation result was taken as the ADCC activity (FIGS. 5A and B). The results show that SW-1C10 exhibits the highest ADCC activity among antibodies compared.

(10) Mass Production of 1C10 for Animal Experiment

Approximately 30,000 1C10 production lines were reared with an artificial diet (Silkmate PS, Nosan Corp.) throughout the entire instars to produce cocoons. The cocoons were each cut with scissors, and pupas were taken out. About 1.1 kg of cocoon shell was obtained. Extraction and purification of SW-1C10 were performed using 1.0 kg of this cocoon shell.

1 kg of cocoon was immersed in 100 L of extraction buffer (50 mM acetic acid buffer solution, pH 5.3, 30 mM NaCl, 0.2% Triton X-100, 0.01% polydimethylsiloxane), and then squeezed at 25° C. for 2 hours to extract protein. The protein was filtrated with a 10 μm-industrial filter (SMC), and then applied to a STREAMLINE 200 Column (GE Healthcare) filled with 5 L of cation exchange carrier (STREAMLINE SP (GE Healthcare)). After washing with a SP washing buffer (50 mM acetic acid buffer solution, pH 5.3, 30 mM NaCl, 0.2% Triton X-100), elution was performed with a SP elution buffer (50 mM acetic acid buffer solution pH 5.3, 300 mM NaCl) to recover a 1C10 antibody. Further, the recovered antibody was concentrated with an ultrafiltration membrane (Biomax-100 TF (Millipore)), and then the solvent was exchanged with PBS. This was applied to a column filled with a protein A carrier (MabSelect SuRe (GE Healthcare)), followed by washing with PBS. Then, a 1C10 antibody was eluted with a 100 mM citric acid buffer solution (pH 3.0). Finally, the eluted antibody was concentrated with an ultrafiltration membrane, and the solvent was exchanged with a preserving solution (10 mM acetic acid buffer solution pH 5.5, 50 mM NaCl, 100 mM arginine hydrochloride). About 7.9 g of purified SW-1C10 with a purity of 99.0% or more was prepared by the above operation.

(11) Administration of 1C10 to HIV-Infected Cynomolgus Monkey

In order to evaluate the effect of SW-1C10 in the acute infection phase, 50,000 TCID50 of strong toxic SHIV89.6P (Reimann K. A. et al., J. Virol. 70, 6922-6928), which is a chimeric virus in which Env derived from the HIV89.6 strain is incorporated into SIV, was inoculated into the rectum of seven cynomolgus monkeys to establish systemic infection. For the group constitution of the cynomolgus monkey, an untreated group as a control consists of four cynomolgus monkeys, and a group administered with SW-1C10 consists of three cynomolgus monkeys. Administration of SW-1C10 was performed via vein on Day 3, Day 10, and Day 17 after virus inoculation, and an effect of suppressing virus in the blood was observed.

The peripheral blood (EDTA was added) was collected from anesthetized monkeys over time, normally, every 7 days until Week 8 after virus inoculation, and thereafter, once every 4 weeks. The plasma was recovered from the collected blood by centrifugation. Then, the hemocyte was diluted with PBS, and overlaid onto Percoll with a specific gravity of 1.070, followed by centrifugation, to separate PBMCs (peripheral blood mononuclear cells). Viral RNA was extracted from the plasma, and the gag region of SIVmac239 was amplified by quantitative RT-PCR. The number of copies of viral RNA in the plasma was calculated from the concentration of the products thereof. The viral RNA in the plasma was extracted and purified by utilizing a MagNA PureCompact Nucleic Acid isolation kit (Roche Diagnosticks).

Calculation of the RNA amount was performed by designing a primer and probe targeting the gag region of SIVmac239, and using a LightCycler 480 thermocycler (Roche Diagnostics). The viral RNA was amplified and detected by using a QuantiTec Probe RT-PCR kit (Qiagen). The followings were designed as a primer and template. That is, as a forward primer, "5'-GCAGAGGAGGAAAT- TACCCAGTAC-3'/SEQ ID NO: 14": as a reverse primer, "5'-CAATTTTACCCAGGCATTTAATGTT-3'/SEQ ID NO: 15"; and as a probe, "5'-FAM-TGTCCACCTGCCAT-TAAGTCCCGA-TAMRA-3'/SEQ ID NO: 16" were respectively used.

Fluorescent detection was performed on the RT-PCR product by a LightCycler 480 thermocycler to determine the amount thereof. The amount of virus in the plasma was determined by performing measurement twice in duplicate and performing conversion using a calibration curve created by serial dilution of SIV RNA of known concentration. Also, the template DNA and other DNA mixed were treated with DNAaseI. The sensitivity of this measurement system was 100 copy/ml.

In the untreated monkey serving as a control, the number of copies of viral RNA in 1 ml of plasma on Week 2 of virus inoculation was raised to several tens of millions to several hundreds of millions of copies, then brought into a stationary state referred to as virological setpoint on Week 8 or later, and shifted by several tens of thousands to several hundreds of thousands copies/ml. The number of CD4+T cells which are an infection target of HIV was rapidly decreased in Week 2 to Week 4, and thereafter, the number of cells was sifted at a lower level. Meanwhile, in the group administered with SW-1C10, the virus amount reached 1 hundred thousand to 1 million copies/ml as a peak on Week 4 of virus inoculation, and then decreased. No virus was detected on Week 12 or later in all the three monkeys. Also, the number of CD4+T cells did not significantly decrease, and the level before virus administration was maintained (FIG. 6).

From these results, surprisingly, the viral load was suppressed to the detection limit or lower in the early stage in all the individuals administered with SW-1C10. The viral RNA load was controlled to the detection limit or lower over a long period of 12 weeks. It has not been no reported in the past that such a control of suppressing viral replication over a long period of time in all administration examples is possible. The present inventors have succeeded in finding, for the first time, an antibody that widely and stably controls the virus relative to administration subject.

The invention claimed is:

1. An IgG antibody that binds to HIV-1 comprising:
   a heavy chain comprising the CDRs as set forth in SEQ ID NOs: 14-16 and a light chain comprising the CDRs as set forth in SEQ. ID NOs: 17-19;
   wherein said IgG antibody further comprises afucosylated glycans.

2. The antibody of claim 1, wherein the antibody has an activity of suppressing HIV-1 load in the blood of an HIV-1 infected patient below the detection limit for an extended period of time.

3. The antibody of claim 1, wherein said heavy chain comprises the amino acid sequence as set forth in SEQ ID NO: 7 and said light chain comprises the amino acid sequence as set forth in SEQ ID NO: 9.

4. The antibody of claim 1, wherein the antibody has a glycan structure selected from the following:

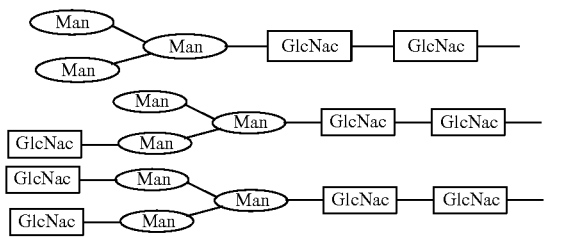

-continued

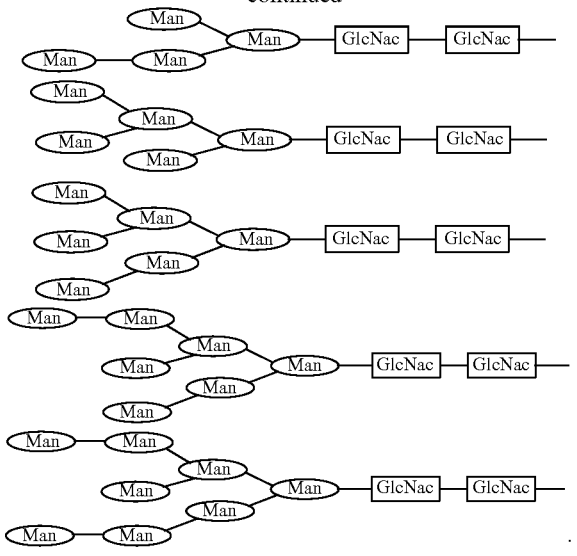

5. The antibody of claim 1, wherein the antibody is produced by a transgenic silkworm.

6. A composition comprising IgG antibodies having the ability to bind HIV-1, wherein 80% or more of the IgG antibodies comprise the antibody of claim 1.

7. An expression cassette comprising any one of the polynucleotides selected from the following (i), (iii) and (v) which is functionally linked to and downstream of a silk gland-specific gene promoter:

(i) a polynucleotide encoding the nucleotide sequence of SEQ ID NO: 6 and/or the nucleotide sequence of SEQ ID NO: 8;

(iii) a polynucleotide encoding the amino acid sequence of SEQ ID NO: 7 and/or a polynucleotide encoding the amino acid sequence of SEQ ID NO: 9; or (v) a polynucleotide encoding an amino acid sequence in which one or more amino acids are substituted in, deleted from, added to, and/or inserted in the amino acid sequence of SEQ ID NO: 7, and/or a polynucleotide encoding an amino acid sequence in which one or more amino acids are substituted in, deleted from, added to, and/or inserted in the amino acid sequence of SEQ ID NO: 9.

8. The expression cassette of claim 7, wherein the promoter is a sericin 1 promoter, a sericin 2 promoter, or a sericin 3 promoter.

9. A plasmid vector comprising the expression cassette of claim 7.

10. A method for producing a transgenic silkworm, the method comprising inserting the plasmid vector of claim 9 into an egg of a silkworm.

11. A transgenic silkworm, wherein the expression cassette of claim 8 is incorporated into a chromosome of the transgenic silkworm.

12. A method for producing an antibody comprising extracting the antibody from silk threads produced by the transgenic silkworm of claim 11.

13. An antibody produced by a transgenic silkworm comprising a heavy chain comprising the amino acid sequence of SEQ ID NO: 11 and a light chain comprising the amino acid sequence of SEQ ID NO: 13.

14. A method for treatment or prevention of HIV-1 infection comprising administering the antibody of claim 1.

15. The method of claim 14, wherein the antibody is administered one to five times after HIV-1 infection.

16. The method of claim 14, wherein the antibody is administered two or more times, and wherein the second and subsequent administrations are performed 3 to 30 days after the previous administration.

17. The antibody of claim 2, wherein the extended period of time is at least 12 weeks.

* * * * *

SEQUENCE LISTING

<160> NUMBER OF SEQ ID NOS: 19

<210> SEQ ID NO 1
<211> LENGTH: 60
<212> TYPE: DNA
<213> ORGANISM: Artificial Sequence
<220> FEATURE:
<223> OTHER INFORMATION: primer

<400> SEQUENCE: 1
atcgcgaaag tattttactg ttttcgtaac agttttgtaa taaaaaaacc tataaatatg      60

<210> SEQ ID NO 2
<211> LENGTH: 42
<212> TYPE: DNA
<213> ORGANISM: Artificial Sequence
<220> FEATURE:
<223> OTHER INFORMATION: primer

<400> SEQUENCE: 2
gtaataaaaa aacctataaa tatggactgg acctggagga tc      42

-continued

```
<210> SEQ ID NO 3
<211> LENGTH: 38
<212> TYPE: DNA
<213> ORGANISM: Artificial Sequence
<220> FEATURE:
<223> OTHER INFORMATION: primer

<400> SEQUENCE: 3
cgctcgagtc gcgattattt acccggagac agggagag                          38

<210> SEQ ID NO 4
<211> LENGTH: 42
<212> TYPE: DNA
<213> ORGANISM: Artificial Sequence
<220> FEATURE:
<223> OTHER INFORMATION: primer

<400> SEQUENCE: 4
gtaataaaaa aacctataaa tatggtgttg cagacccagg tc                     42

<210> SEQ ID NO 5
<211> LENGTH: 39
<212> TYPE: DNA
<213> ORGANISM: Artificial Sequence
<220> FEATURE:
<223> OTHER INFORMATION: primer

<400> SEQUENCE: 5
cgctcgagtc gcgattaaca ctctcccctg ttgaagctc                         39

<210> SEQ ID NO 6
<211> LENGTH: 1425
<212> TYPE: DNA
<213> ORGANISM: Homo sapiens
<220> FEATURE:
<221> NAME/KEY: CDS
<222> LOCATION: (1)..(1425)
<220> FEATURE:
<221> NAME/KEY: sig_peptide
<222> LOCATION: (1)..(57)

<400> SEQUENCE: 6 atg gac tgg acc tgg agg atc ctc ctc ttg gtg gca gca gcc acc ggt      48
Met Asp Trp Thr Trp Arg Ile Leu Leu Leu Val Ala Ala Ala Thr Gly
1               5                   10                  15 gtc cag tgt gag gtg cag ctg gtg gag tct ggg gga ggc gtg gtc cag      96
Val Gln Cys Glu Val Gln Leu Val Glu Ser Gly Gly Gly Val Val Gln
                20                  25                  30 cct ggg agg tcc ctg aga gtc tcc tgt gta gcc tct gga ttc atg ttc     144
Pro Gly Arg Ser Leu Arg Val Ser Cys Val Ala Ser Gly Phe Met Phe
            35                  40                  45 agt aac tat gct atg cac tgg gtc cgc cag act gca ggc aag ggg ctg     192
Ser Asn Tyr Ala Met His Trp Val Arg Gln Thr Ala Gly Lys Gly Leu
        50                  55                  60 gag tgg gtg gct att att tca aat gat gga agc gat aaa tat tac gca     240
Glu Trp Val Ala Ile Ile Ser Asn Asp Gly Ser Asp Lys Tyr Tyr Ala
65                  70                  75                  80 gac tcc gtg cag ggc cga ttc acc gta tct aga gac aac tcc cag aac     288
Asp Ser Val Gln Gly Arg Phe Thr Val Ser Arg Asp Asn Ser Gln Asn
                85                  90                  95 aca ctg ttt ctg caa atg agt ggc ctc aga cct gag gat tcg ggt ctt     336
Thr Leu Phe Leu Gln Met Ser Gly Leu Arg Pro Glu Asp Ser Gly Leu
                100                 105                 110 tat tac tgt gcg aga gat ttg gac cag act att ccg gac ctg act gct     384
Tyr Tyr Cys Ala Arg Asp Leu Asp Gln Thr Ile Pro Asp Leu Thr Ala
```

-continued

```
                115                     120                     125
ccc gct ttt gaa gtc tgg ggc caa ggg aca atg gtc acc gtc tct tca      432
Pro Ala Phe Glu Val Trp Gly Gln Gly Thr Met Val Thr Val Ser Ser
    130                     135                     140 gct agc acc aag ggc cca tcg gtc ttc ccc ctg gca ccc tcc tcc aag      480
Ala Ser Thr Lys Gly Pro Ser Val Phe Pro Leu Ala Pro Ser Ser Lys
145                     150                     155                 160 agc acc tct ggg ggc aca gcg gcc ctg ggc tgc ctg gtc aag gac tac      528
Ser Thr Ser Gly Gly Thr Ala Ala Leu Gly Cys Leu Val Lys Asp Tyr
                    165                     170                 175 ttc ccc gaa ccg gtg acg gtg tcg tgg aac tca ggc gcc ctg acc agc      576
Phe Pro Glu Pro Val Thr Val Ser Trp Asn Ser Gly Ala Leu Thr Ser
                180                     185                 190 ggc gtg cac acc ttc ccg gct gtc cta cag tcc tca gga ctc tac tcc      624
Gly Val His Thr Phe Pro Ala Val Leu Gln Ser Ser Gly Leu Tyr Ser
            195                     200                 205 ctc agc agc gtg gtg acc gtg ccc tcc agc agc ttg ggc acc cag acc      672
Leu Ser Ser Val Val Thr Val Pro Ser Ser Ser Leu Gly Thr Gln Thr
    210                     215                 220 tac atc tgc aac gtg aat cac aag ccc agc aac acc aag gtg gac aag      720
Tyr Ile Cys Asn Val Asn His Lys Pro Ser Asn Thr Lys Val Asp Lys
225                     230                     235             240 aaa gtt gag ccc aaa tct tgt gac aaa act cac aca tgc cca ccg tgc      768
Lys Val Glu Pro Lys Ser Cys Asp Lys Thr His Thr Cys Pro Pro Cys
                    245                     250             255 cca gca cct gaa ctc ctg ggg gga ccg tca gtc ttc ctc ttc ccc cca      816
Pro Ala Pro Glu Leu Leu Gly Gly Pro Ser Val Phe Leu Phe Pro Pro
                260                     265             270 aaa ccc aag gac acc ctc atg atc tcc cgg acc cct gag gtc aca tgc      864
Lys Pro Lys Asp Thr Leu Met Ile Ser Arg Thr Pro Glu Val Thr Cys
            275                     280             285 gtg gtg gtg gac gtg agc cac gaa gac cct gag gtc aag ttc aac tgg      912
Val Val Val Asp Val Ser His Glu Asp Pro Glu Val Lys Phe Asn Trp
    290                     295             300 tac gtg gac ggc gtg gag gtg cat aat gcc aag aca aag ccg cgg gag      960
Tyr Val Asp Gly Val Glu Val His Asn Ala Lys Thr Lys Pro Arg Glu
305                     310             315                 320 gag cag tac aac agc acg tac cgt gtg gtc agc gtc ctc acc gtc ctg      1008
Glu Gln Tyr Asn Ser Thr Tyr Arg Val Val Ser Val Leu Thr Val Leu
                325             330                 335 cac cag gac tgg ctg aat ggc aag gag tac aag tgc aag gtc tcc aac      1056
His Gln Asp Trp Leu Asn Gly Lys Glu Tyr Lys Cys Lys Val Ser Asn
            340             345                 350 aaa gcc ctc cca gcc ccc atc gag aaa acc atc tcc aaa gcc aaa ggg      1104
Lys Ala Leu Pro Ala Pro Ile Glu Lys Thr Ile Ser Lys Ala Lys Gly
        355             360                 365 cag ccc cga gaa cca cag gtg tac acc ctg ccc cca tcc cgg gat gag      1152
Gln Pro Arg Glu Pro Gln Val Tyr Thr Leu Pro Pro Ser Arg Asp Glu
    370             375                 380 ctg acc aag aac cag gtc agc ctg acc tgc ctg gtc aaa ggc ttc tat      1200
Leu Thr Lys Asn Gln Val Ser Leu Thr Cys Leu Val Lys Gly Phe Tyr
385             390                 395                 400 ccc agc gac atc gcc gtg gag tgg gag agc aat ggg cag ccg gag aac      1248
Pro Ser Asp Ile Ala Val Glu Trp Glu Ser Asn Gly Gln Pro Glu Asn
                405                 410                 415 aac tac aag acc acg cct ccc gtg ctg gac tcc gac ggc tcc ttc ttc      1296
Asn Tyr Lys Thr Thr Pro Pro Val Leu Asp Ser Asp Gly Ser Phe Phe
            420                 425                 430 ctc tac agc aag ctc acc gtg gac aag agc agg tgg cag cag ggg aac      1344
```

-continued

```
Leu Tyr Ser Lys Leu Thr Val Asp Lys Ser Arg Trp Gln Gln Gly Asn
        435                 440                 445 gtc ttc tca tgc tcc gtg atg cat gag gct ctg cac aac cac tac acg      1392
Val Phe Ser Cys Ser Val Met His Glu Ala Leu His Asn His Tyr Thr
    450                 455                 460 cag aag agc ctc tcc ctg tct ccg ggt aaa taa                          1425
Gln Lys Ser Leu Ser Leu Ser Pro Gly Lys
465                 470
```

```
<210> SEQ ID NO 7
<211> LENGTH: 474
<212> TYPE: PRT
<213> ORGANISM: Homo sapiens

<400> SEQUENCE: 7

Met Asp Trp Thr Trp Arg Ile Leu Leu Leu Val Ala Ala Ala Thr Gly
1               5                   10                  15

Val Gln Cys Glu Val Gln Leu Val Glu Ser Gly Gly Gly Val Val Gln
            20                  25                  30

Pro Gly Arg Ser Leu Arg Val Ser Cys Val Ala Ser Gly Phe Met Phe
        35                  40                  45

Ser Asn Tyr Ala Met His Trp Val Arg Gln Thr Ala Gly Lys Gly Leu
    50                  55                  60

Glu Trp Val Ala Ile Ile Ser Asn Asp Gly Ser Asp Lys Tyr Tyr Ala
65                  70                  75                  80

Asp Ser Val Gln Gly Arg Phe Thr Val Ser Arg Asp Asn Ser Gln Asn
                85                  90                  95

Thr Leu Phe Leu Gln Met Ser Gly Leu Arg Pro Glu Asp Ser Gly Leu
            100                 105                 110

Tyr Tyr Cys Ala Arg Asp Leu Asp Gln Thr Ile Pro Asp Leu Thr Ala
            115                 120                 125

Pro Ala Phe Glu Val Trp Gly Gln Gly Thr Met Val Thr Val Ser Ser
        130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Gln Thr
        210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
        290                 295                 300

Tyr Val Asp Gly Val Glu Val His Asn Ala Lys Thr Lys Pro Arg Glu
305                 310                 315                 320
```

```
Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Asp Glu
        370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 8
<211> LENGTH: 717
<212> TYPE: DNA
<213> ORGANISM: Homo sapiens
<220> FEATURE:
<221> NAME/KEY: CDS
<222> LOCATION: (1)..(717)
<220> FEATURE:
<221> NAME/KEY: sig_peptide
<222> LOCATION: (1)..(60)

<400> SEQUENCE: 8 atg gtg ttg cag acc cag gtc ttc ata agc ttg ttg ctc tgg atc tct      48
Met Val Leu Gln Thr Gln Val Phe Ile Ser Leu Leu Leu Trp Ile Ser
1               5                   10                  15 ggt gcc tac ggg gat att gtg atg act cag tct cca ctc tcc ctg gcc      96
Gly Ala Tyr Gly Asp Ile Val Met Thr Gln Ser Pro Leu Ser Leu Ala
            20                  25                  30 gtc acc cct gga gag ccg gcc tcc atc tcc tgc agg tct agt cag agc     144
Val Thr Pro Gly Glu Pro Ala Ser Ile Ser Cys Arg Ser Ser Gln Ser
        35                  40                  45 ctc ctg cat agt gat gga aac aat tac ttg gat tgg tat ttg cag aag     192
Leu Leu His Ser Asp Gly Asn Asn Tyr Leu Asp Trp Tyr Leu Gln Lys
    50                  55                  60 cca ggg cag tct cca cag ctc ctg atc tat ttg act tct aat cgg gcc     240
Pro Gly Gln Ser Pro Gln Leu Leu Ile Tyr Leu Thr Ser Asn Arg Ala
65                  70                  75                  80 tcc ggg gtc cct gac agg ttc agt ggc agt gga tca ggc aca gat ttt     288
Ser Gly Val Pro Asp Arg Phe Ser Gly Ser Gly Ser Gly Thr Asp Phe
                85                  90                  95 aca ctg aaa atc agc aga gtg gag gct gag gat gtt ggg gtc tat ttc     336
Thr Leu Lys Ile Ser Arg Val Glu Ala Glu Asp Val Gly Val Tyr Phe
            100                 105                 110 tgc atg caa tct cta caa acc tgg acg ttc ggc caa ggg acc aag gtg     384
Cys Met Gln Ser Leu Gln Thr Trp Thr Phe Gly Gln Gly Thr Lys Val
        115                 120                 125 gaa atc aaa cga act gtg gct gca cca tct gtc ttc atc ttc ccg cca     432
Glu Ile Lys Arg Thr Val Ala Ala Pro Ser Val Phe Ile Phe Pro Pro
        130                 135                 140
```

-continued

```
tct gat gag cag ttg aaa tct gga act gcc tct gtt gtg tgc ctg ctg    480
Ser Asp Glu Gln Leu Lys Ser Gly Thr Ala Ser Val Val Cys Leu Leu
145             150                 155                 160 aat aac ttc tat ccc aga gag gcc aaa gta cag tgg aag gtg gat aac    528
Asn Asn Phe Tyr Pro Arg Glu Ala Lys Val Gln Trp Lys Val Asp Asn
                165                 170                 175 gcc ctc caa tcg ggt aac tcc cag gag agt gtc aca gag cag gac agc    576
Ala Leu Gln Ser Gly Asn Ser Gln Glu Ser Val Thr Glu Gln Asp Ser
            180                 185                 190 aag gac agc acc tac agc ctc agc agc acc ctg acg ctg agc aaa gca    624
Lys Asp Ser Thr Tyr Ser Leu Ser Ser Thr Leu Thr Leu Ser Lys Ala
            195                 200                 205 gac tac gag aaa cac aaa gtc tac gcc tgc gaa gtc acc cat cag ggc    672
Asp Tyr Glu Lys His Lys Val Tyr Ala Cys Glu Val Thr His Gln Gly
        210                 215                 220 ctg agc ttg ccc gtc aca aag agc ttc aac agg gga gag tgt taa       717
Leu Ser Leu Pro Val Thr Lys Ser Phe Asn Arg Gly Glu Cys
225                 230                 235
```

<210> SEQ ID NO 9
<211> LENGTH: 238
<212> TYPE: PRT
<213> ORGANISM: Homo sapiens

<400> SEQUENCE: 9

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Leu Ser Leu Ala
            20                  25                  30

Val Thr Pro Gly Glu Pro Ala Ser Ile Ser Cys Arg Ser Ser Gln Ser
        35                  40                  45

Leu Leu His Ser Asp Gly Asn Asn Tyr Leu Asp Trp Tyr Leu Gln Lys
    50                  55                  60

Pro Gly Gln Ser Pro Gln Leu Leu Ile Tyr Leu Thr Ser Asn Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Phe
            100                 105                 110

Cys Met Gln Ser Leu Gln Thr Trp Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145             150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Leu Pro Val Thr Lys Ser Phe Asn Arg Gly Glu Cys
225                 230                 235
```

-continued

<210> SEQ ID NO 10
<211> LENGTH: 1419
<212> TYPE: DNA
<213> ORGANISM: Homo sapiens
<220> FEATURE:
<221> NAME/KEY: CDS
<222> LOCATION: (1)..(1419)
<220> FEATURE:
<221> NAME/KEY: sig_peptide
<222> LOCATION: (1)..(57)

<400> SEQUENCE: 10

```
atg gac tgg acc tgg agg atc ctc ctc ttg gtg gca gca gcc acc ggt        48
Met Asp Trp Thr Trp Arg Ile Leu Leu Leu Val Ala Ala Ala Thr Gly
1               5                   10                  15 gtc cag tgt gag gtg cac ctg gtg gag tct ggg gga ggc gtg gtc cag        96
Val Gln Cys Glu Val His Leu Val Glu Ser Gly Gly Gly Val Val Gln
                20                  25                  30 cct ggg agg tcc ctg aga ctc tcc tgt gaa gtc tct gga gtc acc ttc       144
Pro Gly Arg Ser Leu Arg Leu Ser Cys Glu Val Ser Gly Val Thr Phe
            35                  40                  45 act gag tct att atg cat tgg ctc cgc cag gct cca ggc aag ggg ccg       192
Thr Glu Ser Ile Met His Trp Leu Arg Gln Ala Pro Gly Lys Gly Pro
        50                  55                  60 gag tgg ctg gca att att tca caa gat gga gcc act aaa ttc tat gca       240
Glu Trp Leu Ala Ile Ile Ser Gln Asp Gly Ala Thr Lys Phe Tyr Ala
65                  70                  75                  80 gac tcc gtg aag ggc cga ttc gcc atc tcc aga gac aat tcc aag aat       288
Asp Ser Val Lys Gly Arg Phe Ala Ile Ser Arg Asp Asn Ser Lys Asn
                85                  90                  95 acg gtg tat ttg gaa atg aac agc ctg aga att gag gac tcg ggt acc       336
Thr Val Tyr Leu Glu Met Asn Ser Leu Arg Ile Glu Asp Ser Gly Thr
                100                 105                 110 tat tac tgt gcg aaa gac ggg gca gat gtg gac aat tta ggt ccc gcc       384
Tyr Tyr Cys Ala Lys Asp Gly Ala Asp Val Asp Asn Leu Gly Pro Ala
            115                 120                 125 ttt gac tac tgg ggc cgg gga acc ctg gtc acc gtc tct tca gct agc       432
Phe Asp Tyr Trp Gly Arg Gly Thr Leu Val Thr Val Ser Ser Ala Ser
        130                 135                 140 acc aag ggc cca tcg gtc ttc ccc ctg gca ccc tcc tcc aag agc acc       480
Thr Lys Gly Pro Ser Val Phe Pro Leu Ala Pro Ser Ser Lys Ser Thr
145                 150                 155                 160 tct ggg ggc aca gcg gcc ctg ggc tgc ctg gtc aag gac tac ttc ccc       528
Ser Gly Gly Thr Ala Ala Leu Gly Cys Leu Val Lys Asp Tyr Phe Pro
                165                 170                 175 gaa ccg gtg acg gtg tcg tgg aac tca ggc gcc ctg acc agc ggc gtg       576
Glu Pro Val Thr Val Ser Trp Asn Ser Gly Ala Leu Thr Ser Gly Val
                180                 185                 190 cac acc ttc ccg gct gtc cta cag tcc tca gga ctc tac tcc ctc agc       624
His Thr Phe Pro Ala Val Leu Gln Ser Ser Gly Leu Tyr Ser Leu Ser
            195                 200                 205 agc gtg gtg acc gtg ccc tcc agc agc ttg ggc acc cag acc tac atc       672
Ser Val Val Thr Val Pro Ser Ser Ser Leu Gly Thr Gln Thr Tyr Ile
            210                 215                 220 tgc aac gtg aat cac aag ccc agc aac acc aag gtg gac aag aaa gtt       720
Cys Asn Val Asn His Lys Pro Ser Asn Thr Lys Val Asp Lys Lys Val
225                 230                 235                 240 gag ccc aaa tct tgt gac aaa act cac aca tgc cca ccg tgc cca gca       768
Glu Pro Lys Ser Cys Asp Lys Thr His Thr Cys Pro Pro Cys Pro Ala
                245                 250                 255 cct gaa ctc ctg ggg gga ccg tca gtc ttc ctc ttc ccc cca aaa ccc       816
Pro Glu Leu Leu Gly Gly Pro Ser Val Phe Leu Phe Pro Pro Lys Pro
```

-continued

```
                260                265                270
aag gac acc ctc atg atc tcc cgg acc cct gag gtc aca tgc gtg gtg     864
Lys Asp Thr Leu Met Ile Ser Arg Thr Pro Glu Val Thr Cys Val Val
        275                280                285 gtg gac gtg agc cac gaa gac cct gag gtc aag ttc aac tgg tac gtg     912
Val Asp Val Ser His Glu Asp Pro Glu Val Lys Phe Asn Trp Tyr Val
    290                295                300 gac ggc gtg gag gtg cat aat gcc aag aca aag ccg cgg gag gag cag     960
Asp Gly Val Glu Val His Asn Ala Lys Thr Lys Pro Arg Glu Glu Gln
305                310                315                320 tac aac agc acg tac cgt gtg gtc agc gtc ctc acc gtc ctg cac cag    1008
Tyr Asn Ser Thr Tyr Arg Val Val Ser Val Leu Thr Val Leu His Gln
                325                330                335 gac tgg ctg aat ggc aag gag tac aag tgc aag gtc tcc aac aaa gcc    1056
Asp Trp Leu Asn Gly Lys Glu Tyr Lys Cys Lys Val Ser Asn Lys Ala
        340                345                350 ctc cca gcc ccc atc gag aaa acc atc tcc aaa gcc aaa ggg cag ccc    1104
Leu Pro Ala Pro Ile Glu Lys Thr Ile Ser Lys Ala Lys Gly Gln Pro
        355                360                365 cga gaa cca cag gtg tac acc ctg ccc cca tcc cgg gat gag ctg acc    1152
Arg Glu Pro Gln Val Tyr Thr Leu Pro Pro Ser Arg Asp Glu Leu Thr
    370                375                380 aag aac cag gtc agc ctg acc tgc ctg gtc aaa ggc ttc tat ccc agc    1200
Lys Asn Gln Val Ser Leu Thr Cys Leu Val Lys Gly Phe Tyr Pro Ser
385                390                395                400 gac atc gcc gtg gag tgg gag agc aat ggg cag ccg gag aac aac tac    1248
Asp Ile Ala Val Glu Trp Glu Ser Asn Gly Gln Pro Glu Asn Asn Tyr
                405                410                415 aag acc acg cct ccc gtg ctg gac tcc gac ggc tcc ttc ttc ctc tac    1296
Lys Thr Thr Pro Pro Val Leu Asp Ser Asp Gly Ser Phe Phe Leu Tyr
                420                425                430 agc aag ctc acc gtg gac aag agc agg tgg cag cag ggg aac gtc ttc    1344
Ser Lys Leu Thr Val Asp Lys Ser Arg Trp Gln Gln Gly Asn Val Phe
        435                440                445 tca tgc tcc gtg atg cat gag gct ctg cac aac cac tac acg cag aag    1392
Ser Cys Ser Val Met His Glu Ala Leu His Asn His Tyr Thr Gln Lys
    450                455                460 agc ctc tcc ctg tct ccg ggt aaa taa                                 1419
Ser Leu Ser Leu Ser Pro Gly Lys
465                470
```

```
<210> SEQ ID NO 11
<211> LENGTH: 472
<212> TYPE: PRT
<213> ORGANISM: Homo sapiens

<400> SEQUENCE: 11

Met Asp Trp Thr Trp Arg Ile Leu Leu Leu Val Ala Ala Ala Thr Gly
1               5                   10                  15

Val Gln Cys Glu Val His Leu Val Glu Ser Gly Gly Val Val Gln
        20                  25                  30

Pro Gly Arg Ser Leu Arg Leu Ser Cys Glu Val Ser Gly Val Thr Phe
        35                  40                  45

Thr Glu Ser Ile Met His Trp Leu Arg Gln Ala Pro Gly Lys Gly Pro
    50                  55                  60

Glu Trp Leu Ala Ile Ile Ser Gln Asp Gly Ala Thr Lys Phe Tyr Ala
65                  70                  75                  80

Asp Ser Val Lys Gly Arg Phe Ala Ile Ser Arg Asp Asn Ser Lys Asn
                85                  90                  95
```

-continued

```
Thr Val Tyr Leu Glu Met Asn Ser Leu Arg Ile Glu Asp Ser Gly Thr
        100                 105                 110

Tyr Tyr Cys Ala Lys Asp Gly Ala Asp Val Asp Asn Leu Gly Pro Ala
        115                 120                 125

Phe Asp Tyr Trp Gly Arg Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470
```

```
<210> SEQ ID NO 12
<211> LENGTH: 717
<212> TYPE: DNA
<213> ORGANISM: Homo sapiens
<220> FEATURE:
```

-continued

```
<221> NAME/KEY: CDS
<222> LOCATION: (1)..(717)
<220> FEATURE:
<221> NAME/KEY: sig_peptide
<222> LOCATION: (1)..(60)

<400> SEQUENCE: 12 atg gtg ttg cag acc cag gtc ttc ata agc ttg ttg ctc tgg atc tct        48
Met Val Leu Gln Thr Gln Val Phe Ile Ser Leu Leu Leu Trp Ile Ser
1               5                   10                  15 ggt gcc tac ggg gat att gtg atg act cag tct cca ctc tcc ctg ccc        96
Gly Ala Tyr Gly Asp Ile Val Met Thr Gln Ser Pro Leu Ser Leu Pro
                20                  25                  30 gtc aac cct gga gag ccg gcc tcc atc tcc tgc agg tct agt cag agc       144
Val Asn Pro Gly Glu Pro Ala Ser Ile Ser Cys Arg Ser Ser Gln Ser
            35                  40                  45 ctc cta cat act aat gga tac aac tat ttg gat tgg tac gtg cag aag       192
Leu Leu His Thr Asn Gly Tyr Asn Tyr Leu Asp Trp Tyr Val Gln Lys
        50                  55                  60 cca ggg cag tct ccg cag ctc ctg atc ttt ttg ggt tct cat cgg gcc       240
Pro Gly Gln Ser Pro Gln Leu Leu Ile Phe Leu Gly Ser His Arg Ala
65                  70                  75                  80 tcc ggg gtc cct gac agg ttc agt ggc agt gga tca ggc aca gat ttt       288
Ser Gly Val Pro Asp Arg Phe Ser Gly Ser Gly Ser Gly Thr Asp Phe
                85                  90                  95 aca ctg aaa atc agc aga gtg gag tct gag gat gtt ggc gtt tat tac       336
Thr Leu Lys Ile Ser Arg Val Glu Ser Glu Asp Val Gly Val Tyr Tyr
            100                 105                 110 tgc atg caa cct cta caa tcg tgg acg ttc ggc caa ggg acc agg gtg       384
Cys Met Gln Pro Leu Gln Ser Trp Thr Phe Gly Gln Gly Thr Arg Val
        115                 120                 125 gaa atc aat cga act gtg gct gca cca tct gtc ttc atc ttc ccg cca       432
Glu Ile Asn Arg Thr Val Ala Ala Pro Ser Val Phe Ile Phe Pro Pro
        130                 135                 140 tct gat gag cag ttg aaa tct gga act gcc tct gtt gtg tgc ctg ctg       480
Ser Asp Glu Gln Leu Lys Ser Gly Thr Ala Ser Val Val Cys Leu Leu
145                 150                 155                 160 aat aac ttc tat ccc aga gag gcc aaa gta cag tgg aag gtg gat aac       528
Asn Asn Phe Tyr Pro Arg Glu Ala Lys Val Gln Trp Lys Val Asp Asn
                165                 170                 175 gcc ctc caa tcg ggt aac tcc cag gag agt gtc aca gag cag gac agc       576
Ala Leu Gln Ser Gly Asn Ser Gln Glu Ser Val Thr Glu Gln Asp Ser
            180                 185                 190 aag gac agc acc tac agc ctc agc agc acc ctg acg ctg agc aaa gca       624
Lys Asp Ser Thr Tyr Ser Leu Ser Ser Thr Leu Thr Leu Ser Lys Ala
        195                 200                 205 gac tac gag aaa cac aaa gtc tac gcc tgc gaa gtc acc cat cag ggc       672
Asp Tyr Glu Lys His Lys Val Tyr Ala Cys Glu Val Thr His Gln Gly
        210                 215                 220 ctg agc ttg ccc gtc aca aag agc ttc aac agg gga gag tgt taa          717
Leu Ser Leu Pro Val Thr Lys Ser Phe Asn Arg Gly Glu Cys
225                 230                 235

<210> SEQ ID NO 13
<211> LENGTH: 238
<212> TYPE: PRT
<213> ORGANISM: Homo sapiens

<400> SEQUENCE: 13

Met Val Leu Gln Thr Gln Val Phe Ile Ser Leu Leu Leu Trp Ile Ser
1               5                   10                  15
```

-continued

```
Gly Ala Tyr Gly Asp Ile Val Met Thr Gln Ser Pro Leu Ser Leu Pro
             20                  25                  30

Val Asn Pro Gly Glu Pro Ala Ser Ile Ser Cys Arg Ser Ser Gln Ser
         35                  40                  45

Leu Leu His Thr Asn Gly Tyr Asn Tyr Leu Asp Trp Tyr Val Gln Lys
     50                  55                  60

Pro Gly Gln Ser Pro Gln Leu Leu Ile Phe Leu Gly Ser His Arg Ala
65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ser Glu Asp Val Gly Val Tyr Tyr
             100                 105                 110

Cys Met Gln Pro Leu Gln Ser Trp Thr Phe Gly Gln Gly Thr Arg Val
         115                 120                 125

Glu Ile Asn Arg Thr Val Ala Ala Pro Ser Val Phe Ile Phe Pro Pro
     130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                 165                 170                 175

Ala Leu Gln Ser Gly Asn Ser Gln Glu Ser Val Thr Glu Gln Asp Ser
             180                 185                 190

Lys Asp Ser Thr Tyr Ser Leu Ser Ser Thr Leu Thr Leu Ser Lys Ala
             195                 200                 205

Asp Tyr Glu Lys His Lys Val Tyr Ala Cys Glu Val Thr His Gln Gly
     210                 215                 220

Leu Ser Leu Pro Val Thr Lys Ser Phe Asn Arg Gly Glu Cys
225                 230                 235

<210> SEQ ID NO 14
<211> LENGTH: 8
<212> TYPE: PRT
<213> ORGANISM: Artificial Sequence
<220> FEATURE:
<223> OTHER INFORMATION: CDRH1

<400> SEQUENCE: 14

Gly Phe Met Phe Ser Asn Tyr Ala
1               5

<210> SEQ ID NO 15
<211> LENGTH: 8
<212> TYPE: PRT
<213> ORGANISM: Artificial Sequence
<220> FEATURE:
<223> OTHER INFORMATION: CDRH2

<400> SEQUENCE: 15

Ile Ser Asn Asp Gly Ser Asp Lys
1               5

<210> SEQ ID NO 16
<211> LENGTH: 19
<212> TYPE: PRT
<213> ORGANISM: Artificial Sequence
<220> FEATURE:
<223> OTHER INFORMATION: CDRH3

<400> SEQUENCE: 16

Cys Ala Arg Asp Leu Asp Gln Thr Ile Pro Asp Leu Thr Ala Pro Ala
```

-continued

```
1               5               10              15

Phe Glu Val

<210> SEQ ID NO 17
<211> LENGTH: 10
<212> TYPE: PRT
<213> ORGANISM: Artificial Sequence
<220> FEATURE:
<223> OTHER INFORMATION: CDRL1

<400> SEQUENCE: 17

Gln Ser Leu Leu His Ser Asp Gly Asn Asn
1               5                    10

<210> SEQ ID NO 18
<211> LENGTH: 3
<212> TYPE: PRT
<213> ORGANISM: Artificial Sequence
<220> FEATURE:
<223> OTHER INFORMATION: CDRL2

<400> SEQUENCE: 18

Leu Thr Ser
1

<210> SEQ ID NO 19
<211> LENGTH: 8
<212> TYPE: PRT
<213> ORGANISM: Artificial Sequence
<220> FEATURE:
<223> OTHER INFORMATION: CDRL3

<400> SEQUENCE: 19

Met Gln Ser Leu Gln Thr Trp Thr
1               5
```